(12) United States Patent
Wu et al.

(10) Patent No.: US 7,118,558 B2
(45) Date of Patent: Oct. 10, 2006

(54) CLOTH-LIKE LAMINATE AND ABSORBENT GARMENT

(75) Inventors: Lanying Z. Wu, Paoli, PA (US); Joseph B. Vergona, Suwanee, GA (US); Ruth L. Levy, Collegeville, PA (US); Edward P. Erdman, Chester, PA (US); Stacy J. Driskell, Royersford, PA (US)

(73) Assignee: Tyco Healthcare Retail Services AG, (CH)

( * ) Notice: Subject to any disclaimer, the term of this patent is extended or adjusted under 35 U.S.C. 154(b) by 339 days.

(21) Appl. No.: 10/668,502

(22) Filed: Sep. 24, 2003

(65) Prior Publication Data
US 2004/0158217 A1    Aug. 12, 2004

Related U.S. Application Data

(63) Continuation-in-part of application No. 09/985,885, filed on Nov. 6, 2001, now abandoned.

(51) Int. Cl.
*A61F 13/20* (2006.01)
(52) U.S. Cl. .............................. 604/385.29; 604/385.3
(58) Field of Classification Search .......... 604/385.01, 604/385.24, 385.29, 385.3, 385.22, 386, 604/394
See application file for complete search history.

(56) References Cited

U.S. PATENT DOCUMENTS

| | | |
|---|---|---|
| 2,866,459 A | 12/1958 | Sobelson |
| 3,860,003 A | 1/1975 | Buell |
| 4,081,301 A | 3/1978 | Buell |
| 4,205,679 A | 6/1980 | Repke et al. |
| D257,884 S | 1/1981 | Ternstrom |
| 4,515,595 A | 5/1985 | Kievit et al. |
| 4,610,678 A | 9/1986 | Weisman et al. |
| 4,641,381 A | 2/1987 | Heran et al. |
| 4,687,477 A | 8/1987 | Suzuki |
| 4,695,278 A | 9/1987 | Lawson |
| 4,743,241 A | 5/1988 | Igaue |
| 4,771,483 A | 9/1988 | Hooreman et al. |
| 4,795,454 A | 1/1989 | Dragoo |
| 4,808,177 A | 2/1989 | DesMarais et al. |
| 4,815,660 A | 3/1989 | Boger |
| 4,816,025 A | 3/1989 | Foreman |
| 4,846,825 A | 7/1989 | Enloe |

(Continued)

FOREIGN PATENT DOCUMENTS

GB    2 118 021 A   *  10/1983

(Continued)

*Primary Examiner*—Tatyana Zalukaeva
*Assistant Examiner*—Michael Bogart
(74) *Attorney, Agent, or Firm*—Gosz & Partners LLP

(57) ABSTRACT

An elastic assembly for absorbent garments having a first carrier layer, a second carrier layer, and an elastic layer attached between the first and second carrier layers to impart elasticity to an elasticized portion of the elastic assembly. The elastic layer is made of elastic strands having a decitex of about 600 or less. The elastic strands are arranged generally in parallel with one another and with a spacing of about 1 to about 10 elastic strands per centimeter. The elasticized portion of the elastic assembly has a thickness of about 2.6 mm or less at a pressure of 0.05 p.s.i. and about 8 or more corrugations per centimeter when in an elastically relaxed state. The first and second carrier layers are attached to one another in the elasticized portion substantially only by a coating of adhesive on the elastic strands. Absorbent garments incorporating the elastic assembly and a method of making the elastic assembly are also provided.

30 Claims, 12 Drawing Sheets

U.S. PATENT DOCUMENTS

| | | | |
|---|---|---|---|
| 4,917,696 A | 4/1990 | De Jonckheere | |
| 4,919,738 A | 4/1990 | Ball et al. | |
| 4,938,753 A | 7/1990 | Van Gompel et al. | |
| 4,938,755 A | 7/1990 | Foreman | |
| 4,938,757 A | 7/1990 | Van Gompel et al. | |
| 4,940,464 A | 7/1990 | Van Gompel et al. | |
| 5,037,415 A | 8/1991 | Leroy | |
| 5,137,537 A | 8/1992 | Herron et al. | |
| 5,147,345 A | 9/1992 | Young et al. | |
| 5,275,590 A | 1/1994 | Huffman et al. | |
| 5,281,207 A | 1/1994 | Chmielewski et al. | |
| 5,403,301 A | 4/1995 | Huffman | |
| 5,413,654 A * | 5/1995 | Igaue et al. | 156/161 |
| 5,415,649 A | 5/1995 | Watanabe | |
| 5,439,458 A | 8/1995 | Noel et al. | |
| 5,449,353 A | 9/1995 | Wantanabe et al. | |
| 5,545,158 A * | 8/1996 | Jessup | 604/385.3 |
| 5,554,145 A | 9/1996 | Roe et al. | |
| 5,569,232 A | 10/1996 | Roe et al. | |
| 5,569,234 A | 10/1996 | Buell et al. | |
| 5,634,917 A | 6/1997 | Fujioka et al. | |
| 5,643,243 A | 7/1997 | Klemp | |
| 5,660,664 A | 8/1997 | Herrmann | |
| RE35,687 E | 12/1997 | Igaue et al. | |
| 5,749,865 A | 5/1998 | Yamamoto et al. | |
| 5,836,931 A | 11/1998 | Toyoda et al. | |
| 5,870,778 A | 2/1999 | Tharpe | |
| 5,993,433 A | 11/1999 | St. Louis et al. | |
| 6,235,137 B1 | 5/2001 | Van Eperen et al. | |
| 6,336,922 B1 * | 1/2002 | VanGompel et al. | 604/385.3 |
| 2002/0045878 A1 * | 4/2002 | Shimoe et al. | 604/391 |
| 2004/0122411 A1 * | 6/2004 | Hancock-Cooke | 604/385.29 |

FOREIGN PATENT DOCUMENTS

| | | |
|---|---|---|
| GB | 2268389 | 1/1994 |
| JP | 3-231660 | 10/1991 |
| JP | 4-161152 | 6/1992 |
| JP | 6-197920 | 7/1994 |
| WO | WO 93/24085 | 12/1993 |
| WO | WO 94/09736 | 5/1994 |
| WO | WO 94/28845 | 12/1994 |
| WO | WO 96/05788 | 2/1996 |
| WO | WO 96/23468 | 8/1996 |
| WO | WO 99/13813 | 3/1999 |

* cited by examiner

CLOTH-LIKE LAMINATE AND ABSORBENT GARMENT

CROSS REFERENCE TO RELATED APPLICATION

This application is a continuation-in-part of U. S. application Ser. No. 09/985,885, filed Nov. 6, 2001, now abandoned, the disclosure of which is incorporated herein by reference in its entirety.

BACKGROUND OF THE INVENTION

1. Field of the Invention

The invention relates to the field of absorbent garments in general, and more particularly to an elastic laminate that can be incorporated into absorbent garments to provide cloth-like elastic regions having improved fit and aesthetics.

2. Description of Related Art

Disposable absorbent garments such as infant diapers or training pants, adult incontinence products, and other such products are well-known in the art. Typically, the chassis of such garments comprises a liquid-permeable body-contacting liner sheet (or "topsheet"), a liquid-impermeable backing sheet (or "backsheet") (collectively the "sheets"), and a moisture-absorbent core fiber (or "absorbent core") that usually is made of a mat of randomly arrayed cellulose fiber and is generally disposed between the topsheet and the backsheet. These garments oftentimes incorporate elastic elements in the waist, stomach, and leg areas for improving the fit of the garment. The waist and stomach elastic elements increase the flexibility of the garment, allowing the same garment to accommodate a greater range of body sizes. In addition, they make the garment more form-fitting for the wearer. Leg gather elastic elements and standing leg gathers have also been employed to help reduce leakage of urinary and bowel movement ("BM") from the garment when the absorbent cores cannot absorb body exudates fast enough. Leg gathers are known in the art, and U.S. Pat. No. 5,660,664 issued to Herrmann, the disclosure of which is incorporated by reference herein in its entirety, discloses an exemplary method of manufacturing leg gathers.

These garments typically are prepared by continuously supplying the various components of the garment, and forming these components into the final garment. The elastic elements are continuously supplied at several different points of the assembly process, and are coated with adhesive prior to bonding to the garment components.

Methods of bonding elastics to garment materials have been previously discussed in the art. An example of disposing elastic elements between layers of sheet material is given in U.S. Pat. No. 5,870,778 issued to Tharpe, the disclosure of which is incorporated by reference herein in its entirety. Tharpe discloses coating the garment materials with adhesive to affix the elastic elements therein. A common procedure for affixing elastic elements in the industry today is a spiral spray adhesive application as disclosed in U.S. Pat. No. 4,815,660, issued to Boger, the disclosure of which is incorporated by reference herein in its entirety. Spiral spray adhesive application consists of ejecting a bead of hot melt adhesive, directing jets of pressurized air to form an elongated adhesive fiber from the bead, and imparting a rotational motion to the adhesive fiber. The spirals of adhesive are then deposited on the target substrate, here elastic elements, which are then associated with the garment materials. In usage, the adhesive spray coats not only the elastic elements but also "oversprays" to other sites, causing a number of undesirable consequences.

First, the garment materials that are "oversprayed," e.g., portions of the topsheet, the bottom sheet, and the absorbent core, become rigid upon hardening of the "oversprayed" adhesive making the garment less comfortable for its wearer. This has been referred to as the "plywood effect." Second, the "overspray" coats parts of the assembly machinery that must then be periodically cleaned of the adhesive. Third, the elastic elements may not be uniformly coated with the adhesive due to the nature of the spraying operation, and therefore the elastic elements may not bond to the garment materials as well as if they had been more uniformly and completely coated with the adhesive. Finally, the "overspray" is wasted adhesive, increasing the cost of materials for the finished garment.

Previous attempts have been made to reduce the amount of excess adhesive that is applied to the garment, but these efforts have proved inadequate for reducing garment stiffening caused by the "plywood effect" and for reducing the cost of the garment due to excessive adhesive use. U.S. Pat. No. 5,993,433 issued to St. Louis et al., which is incorporated herein by reference in its entirety, discloses an adhesive pattern for applying adhesives to the gathers, but such adhesive patterns still contribute to excessive garment stiffness and cost. U.S. Pat. No. 6,235,137 issued to Van Eperen et al., which is incorporated herein by reference in its entirety, discloses a method of coating an elastic strand with a filament of adhesive, but this coating process is still subject to overspraying, and does not provide a complete coating of adhesive on the elastic.

Previous attempts to incorporate elastic materials into absorbent garments have also failed to simulate cloth-like materials, both with regard to aesthetic desirability and comfort and fit. For example, garments having spaced elastic strands, provide a heavily corrugated appearance and fit that allows the elastic strands to press against the wearer in such a way that comfort and fit are sacrificed. Other garments have replaced the elastic strands with an elastic film that simulates cloth materials in appearance and fit better than spaced elastic strands, but still fail to provide the desirable breathability characteristics of cloth, which are better provided by constructions having spaced-apart elastic strands. In still other garments, elastic strands have been sandwiched between nonwoven layers, but the layers have been bonded to one another by heat bonding or adhesives, causing the overall laminate structure to be rigid and uncomfortable to wear. The problems associated with these prior art constructions are particularly manifest in the waist-encircling side panels of absorbent garments, which define, in large part, the overall look and feel of absorbent garments.

Accordingly, there exists a need to provide an elastic laminate that can be incorporated into absorbent garments to provide a cloth-like look and feel, improved comfort and fit, and maintain the high breathability of spaced elastic strand constructions.

SUMMARY OF THE INVENTION

In response to these and other deficiencies in the prior art, the present invention provides an elastic assembly for absorbent garments, a method for forming an elastic assembly, and a garment incorporating the elastic assembly. The elastic assembly has a first carrier layer, a second carrier layer, and an elastic layer. The elastic layer is attached between the first and second carrier layers to impart elasticity to an elasticized portion of the elastic assembly. The elastic layer comprises elastic strands, and the first and second carrier layers are attached to one another in the elasticized portion substantially only by a coating of adhesive on the elastic strands.

The elastic strands have a decitex of about 600 or less, or, in other embodiments, about 220 decitex or less. The elastic strands are arranged generally in parallel with one another and with a spacing of about 1 to about 10 elastic strands per centimeter, or, in other embodiments, about 4 elastic strands per centimeter.

The elasticized portion of the elastic assembly has a thickness of about 2.6 mm or less at a pressure of 0.05 p.s.i. when the elasticized portion is in an elastically relaxed state, and, in other embodiments, also may have a thickness of about 2.2 mm or less at a pressure of 0.12 p.s.i. when relaxed. In an embodiment in which the elastic assembly is installed in a garment, the elasticized portion of the elastic assembly (which may include a chassis layer to which it is attached) has a thickness of about 3.6 mm or less at a pressure of 0.05 p.s.i. when the elasticized portion is in an elastically relaxed state, and, in other embodiments, also may have a thickness of about 3.2 mm or less at a pressure of 0.12 p.s.i. when relaxed.

The elasticized portion of the elastic assembly has about 8 or more corrugations per centimeter when in an elastically relaxed state. In an embodiment in which the elastic assembly is installed in a garment, the elasticized portion of the elastic assembly (which may include a chassis layer to which it is attached) may have 8 or more corrugations per centimeter on an body-facing side, and about 10 or more corrugations per centimeter on an outward-facing side.

In one embodiment, the coating of adhesive on the elastic strands may comprise about 0.0180 grams or less of adhesive per linear meter of each elastic strand, or, in another embodiment, about 0.0121 grams or less of adhesive per linear meter of each elastic strand. In another embodiment, the elastic assembly has a width of about 8 cm to about 30 cm and the elastic strands comprise about 8 to about 300 elastic strands. In another embodiment the elastic assembly has a width of about 12 cm and the elastic strands comprise about 49 elastic strands. In various other embodiments, the first and second carrier layers may comprise a nonwoven material having a basis weight of less than about 20 gsm or less, or about 13.5 gsm or less. In still other embodiments, the elastic strands may be extended to about 2 times to 4 times their relaxed length when attached between the carrier layers, or they may be extended to about 3.5 times their relaxed length when attached between the carrier layers.

In still another embodiment, the elasticized portion of the elastic assembly may have two elasticized regions with an inelastic region between them. A first portion of the elastic layer is located in the first elasticized region, and a second portion of the elastic layer is located in the second elasticized region. In the inelastic region, a third portion of the elastic layer is located between, but substantially unattached to, the first and second carrier layers. The third portion of the elastic layer is severed, and does not impart any substantial amount of elasticity to the elastic assembly in the inelastic region. In various embodiments, the third portion of the elastic assembly may be severed by an ultrasonic bond, a heat bond, a mechanical bond, a one-dimensional pattern of cuts or a two-dimensional pattern of cuts. In an embodiment in which a two-dimensional pattern of cuts is used to sever the third portion of the elastic layer, the first and second carrier layers may be bonded to one another at substantially each cut.

In an embodiment in which one or more elastic assemblies are used in an absorbent garment, the garment may have a first waist region, a second waist region, and a crotch region extending between the first and second waist regions. The garment also has a core assembly located at least partially within the crotch region. The core assembly has a substantially fluid-pervious body-facing topsheet, a substantially fluid-impervious backsheet and an absorbent core between the topsheet and the backsheet. At least one elastic assembly is located in at least one of the first waist region and second waist region.

In another embodiment in which one or more elastic assemblies are integrated into an absorbent garment, the absorbent garment also may have a chassis layer that forms the first waist region, the second waist region and the crotch region, and the crotch region is laterally narrower than the first and second waist regions. The core assembly is attached at least partially within the crotch region to an inward-facing side of the chassis layer. At least one elastic assembly is attached to an inward facing side of the chassis layer in the first waist region such that the first elasticized portion overlaps a first lateral side of the first waist region and the second elasticized portion overlaps a second lateral side of the first waist region.

In another embodiment, an absorbent garment having an integrated elastic assembly may have a total contracting force of about 3,500 grams to about 4,100 grams. In another such embodiment, the garment has a total contracting force of about 3,850 grams.

In yet another embodiment, the elastic assembly may be integrated into the garment by attaching it to the chassis layer with about 4.50 grams per square meter (gsm) or less of adhesive. In another embodiment, the elastic assembly is attached to the chassis layer by a continuous meltblown fiber pattern of hot melt adhesive.

In some embodiments of the invention, the elastic assembly can be integrated various kinds of absorbent articles, baby training pants, baby diapers, and adult incontinent products.

Still another embodiment of invention provides a method for forming an elastic assembly. The method includes the steps of extending one or more elastic strands; coating the one or more elastic strands with adhesive in a first zone; not coating the one or more elastic strands with adhesive in a second zone; coating the one or more elastic strands with adhesive in a third zone; sandwiching the one or more elastic strands between a first carrier layer and a second carrier layer to thereby form an elasticized laminate having a first glued zone corresponding to the first zone, an unglued zone corresponding to the second zone, and a second glued zone corresponding to the third zone; severing the one or more elastic strands with a two-dimensional pattern of cuts in the unglued zone; and bonding the first carrier layer and second carrier layer together in the unglued zone at substantially all of the cuts. The severing step and the bonding step occur substantially simultaneously.

BRIEF DESCRIPTION OF THE DRAWINGS

The invention may be understood more readily by reference to the accompanying drawings, in which.

DETAILED DESCRIPTION OF THE PREFERRED EMBODIMENTS

"Garment," as used herein, refers to articles and garments that absorb and contain body exudates, and more specifically refers to articles and garments that are placed against or in proximity to the body of the wearer to absorb and contain the various exudates discharged from the user's body. A non-exhaustive list of examples of "absorbent articles" and garments includes diapers, diaper covers, disposable diapers, training pants, feminine hygiene products, and adult incontinence products. The invention can be used with all of the foregoing classes of absorbent articles and garments, without limitation, whether disposable or otherwise. Furthermore, the invention will be understood to encompass, without limitation, all classes and types of absorbent articles and garments, including those described above.

Absorbent garments and diapers may have a number of different constructions. In each of these constructions it is generally the case that an absorbent core is disposed between a liquid pervious, body-facing topsheet, and a liquid impervious, exterior backsheet. In some cases, one or both of the topsheet and backsheet may be shaped to form a pant-like garment. In other cases, the topsheet, backsheet and absorbent core may be formed as a discrete assembly that is placed on a main chassis layer and the chassis layer is shaped to form a pant-like garment. The garment may be provided to the consumer in the fully assembled pant-like shape, or may be partially pant-like and require the consumer to take the final steps necessary to form the final pant-like shape. In the case of training pant-type garments and most adult incontinent products, the garment is provided fully formed with factory-made side seams and the garment is donned by pulling it up the wearer's legs. In the case of diapers, a caregiver usually wraps the diaper around the wearer's waist and joins the side seams manually by attaching one or more adhesive or mechanical tabs, thereby forming a pant-like structure. It will be readily understood by those of ordinary skill in the art that that present invention may be used with any absorbent garment having elastics incorporated therein, including training pants, diapers, convertible diapers, adult incontinence products, and other absorbent garments, whether specifically discussed herein or not.

Figure 1:
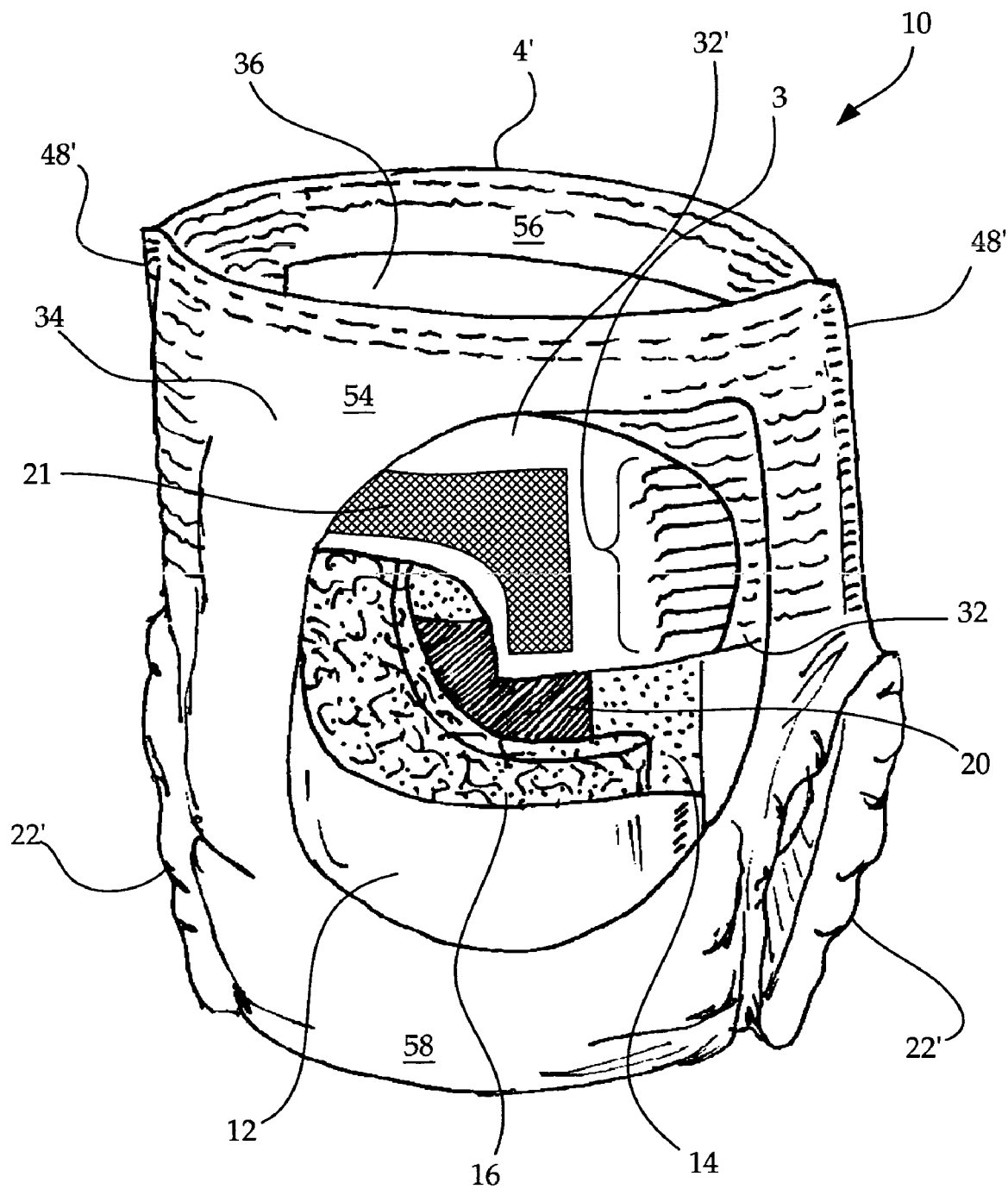
FIG. 1 depicts a garment according to a preferred embodiment of the invention as it appears when worn by a user, with portions of the garment partially cut away to show internal parts.
Figure 2A:
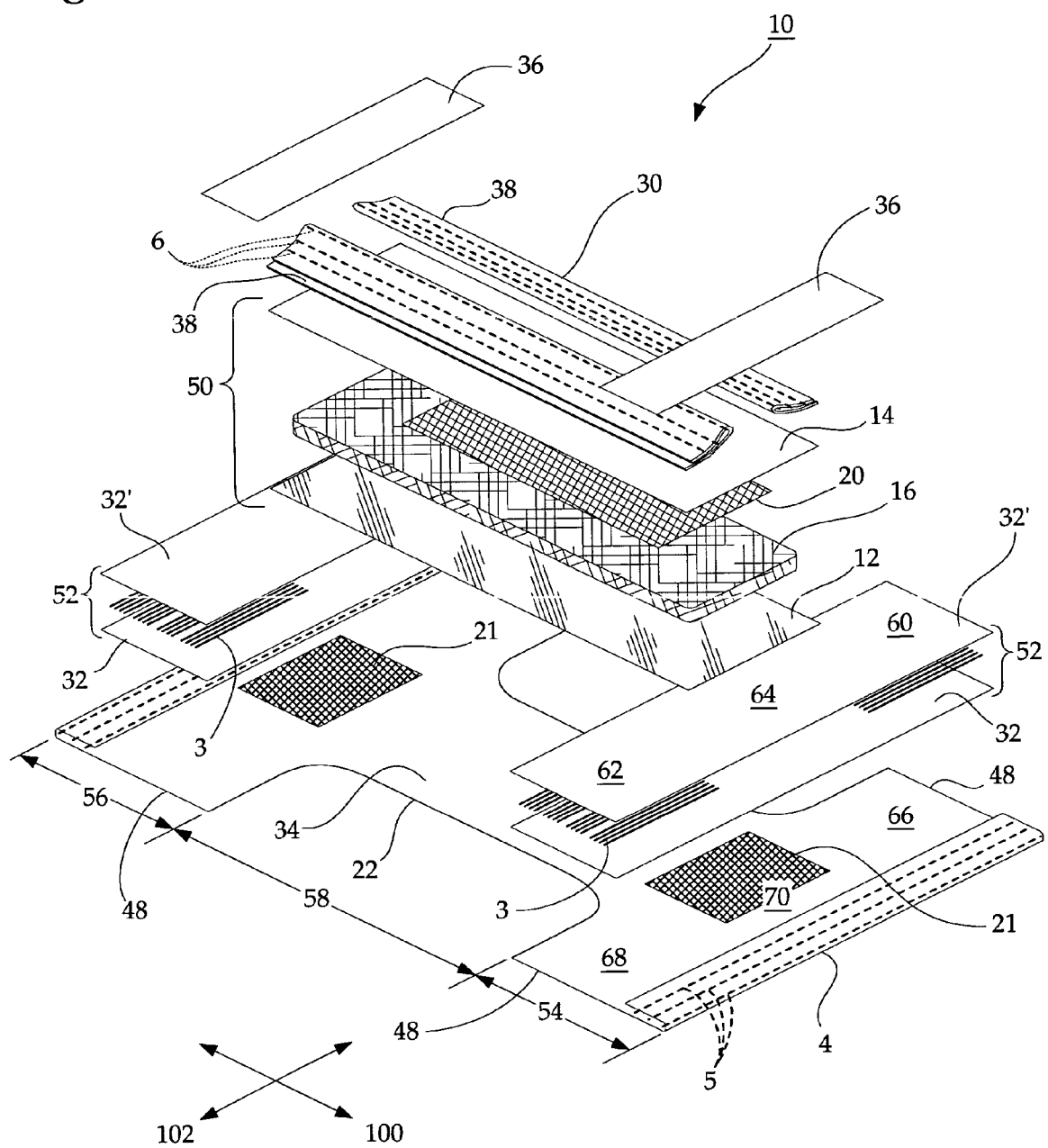
FIG. 2A is an exploded isometric view of the garment of FIG. 1, as shown laid flat with the side seams separated, and with the effects of the elastics removed for purposes of explanation.

The present invention is described generally with reference to FIGS. 1 and 2A. FIG. 1 depicts a preferred embodiment of the present invention as worn. FIG. 2A is an exploded view of a preferred embodiment of the present invention with elastic members shown in the elongated position for clarity, and the garment laid flat. The garment 10 has a longitudinal axis 100 corresponding approximately to the rear-to-front axis of the garment, as it appears when worn by an intended wearer, and a lateral axis 102, orthogonal to the longitudinal axis 100, and corresponding approximately to the side-to-side axis of the garment.

In the embodiment of FIGS. 1 and 2A, the garment 10 comprises a main chassis layer 34 that forms a pant-like garment 10 having two leg holes 22' and a waist encircling edge 4'. The pant-like structure may be formed by joining lateral edge portions 48 to one another to form side seams 48'. The seams 48' may be designed to be torn apart to assist with removing the garment 10. The lateral edge portions 48 may be joined during manufacture by any means known in the art or a combination of such means. Examples of such means include: adhesives such as hot melt adhesives and construction adhesives, chemical or solvent bonding, stitching, ultrasonic bonding, autogenous bonding, and, preferably, heat welding. The lateral edge portions 48 may also be joined by a user with the assistance of adhesive strips or mechanical fasteners (not shown). When the lateral edge portions 48 are joined, leg hole cutouts 22 along the lateral edges of the garment 10 form leg holes 22', and the longitudinal ends 4 of the garment 10 form a waist encircling edge 4'. The garment 10 is divided into a first waist region 54, a second waist region 56, and a crotch region 58 that extends between the first and second waist regions 54, 56.

Figure 2B:
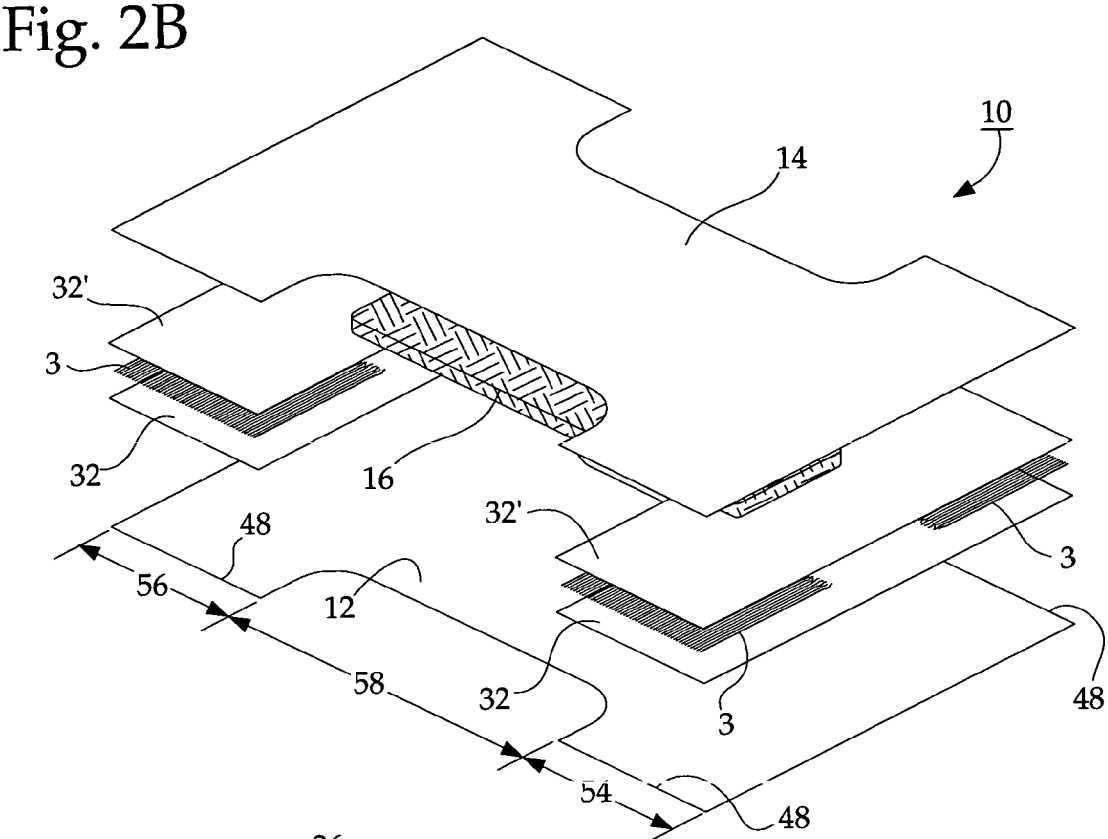
FIG. 2B is an exploded isometric view of another embodiment of the present invention.

A core assembly 50 is disposed on the interior of the chassis layer 34 in the crotch region 58, and may also extend into either waist region 54, 56. The core assembly 50 may comprise an absorbent core 16 disposed between an exterior facing moisture impervious barrier film 12 or "backsheet," and a moisture pervious body-contacting inner layer 14 or "topsheet." Each of the backsheet 12, topsheet 14 and absorbent core 16 may comprise a plurality of layers of materials. In the embodiment depicted in FIG. 1, the backsheet 12, topsheet 14, and absorbent core 16 comprise a subassembly that may be attached to the chassis layer 34. It should be readily apparent that in another preferred embodiment, one or both of the topsheet 14 and backsheet 12 may be shaped to form the main body of a pant-like garment thereby eliminating the need for a separate chassis layer 34. Such an embodiment is shown in FIG. 2B. The backsheet 12, topsheet 14, and absorbent core 16 also may be assembled and used without ever being shaped as a pant-like garment, such as when used as a feminine care product.

The chassis layer 34 may comprise a nonwoven polyethylene or polypropylene sheet or any other suitable garment material known in the art or hereafter discovered. In a preferred embodiment, the chassis layer 34 comprises a nonwoven polypropylene sheet having a spunbond-spunbond construction and a basis weight of about 17 grams per square meter. Such a material is available from PGI Nonwovens Polymer Group Inc. of Mooresville, N.C. All or part of the chassis layer 34 may comprise a liquid pervious or liquid impervious material or a may be zone-treated to be partially liquid pervious or impervious. The chassis layer 34 may be stretched in one or more directions during the manufacturing process, thereby reducing its elasticity in the direction of stretch, as known in the art.

The backsheet 12 may comprise a laminate of multiple layers of materials that have similar or different properties. The backsheet 12 is preferably made from a substantially liquid impervious material to prevent or inhibit the passage of body exudates. The selection and manufacture of such materials is well known in the art, and is disclosed, for example, in U.S. Pat. No. 6,123,694 issued to Peniak et al., and U.S. Pat. No. 6,176,952 issued to Maugans et al., each of which is incorporated herein by reference in its entirety, and in a manner consistent with the present invention. In one embodiment, the backsheet 12 is made from a thin thermoplastic material, such as a pigmented polyethylene film having a thickness in the range of 0.02–0.04 millimeters (mm). The backsheet 12 may also have a laminate construction comprising one or more layers of meltblown polypropylene or meltblown polyethylene, sandwiched between layers of spun-bonded material (often referred to as an "SMS" laminate). Additional layers may be added to the backsheet 12 in order to provide it with other desirable properties, such as to improve the tactile feel, or "hand." The backsheet 12 may also be entirely or partly gas pervious to allow the garment to circulate air, or "breathe." Such breathability may be obtained by perforating or slitting the backsheet, which may reduce the fluid imperviousness of the backsheet by an acceptable amount. The backsheet 12 also may be printed on an inside surface with one or more decorative and/or wetness indicating graphics (not shown). Suitable inks for such graphics are known in the art.

The topsheet 14, which preferably overlays the backsheet 12, can be made from a substantially liquid pervious material to allow body exudates to penetrate into the absorbent core 16. The topsheet 14 may typically comprise a carded polyester fiber with a latex binder or a spun-bonded polypropylene having continuous fibers and thermally bonded by patterned calendar rolls. The topsheet 14 may be treated over all or part of its surface to render it hydrophilic, and may also be zone-treated with a surfactant to render it hydrophilic only in certain target areas. The topsheet 14 may also be treated with skin treating ingredients, such as aloe, vitamin E, and the like, which can be accomplished by a variety of methods known in the art. The topsheet 14 may also comprise an apertured material, such as an apertured film.

In one preferred embodiment of the present invention, one or more of the topsheet 14, backsheet 12 and chassis layer 34 may comprise a laminate of several layers of material, which may have different physical properties. In another embodiment, one or more of the topsheet 14, backsheet 12 and chassis layer 34 may comprise several pieces of material, which may have dissimilar physical properties, joined at or near their edges to form a multi-paneled sheet. Such an embodiment is disclosed, for example, in U.S. Pat. No. 5,275,590 issued to Huffman et al., which is incorporated herein by reference in its entirety, and in a manner consistent with the present invention.

Figure 2C:
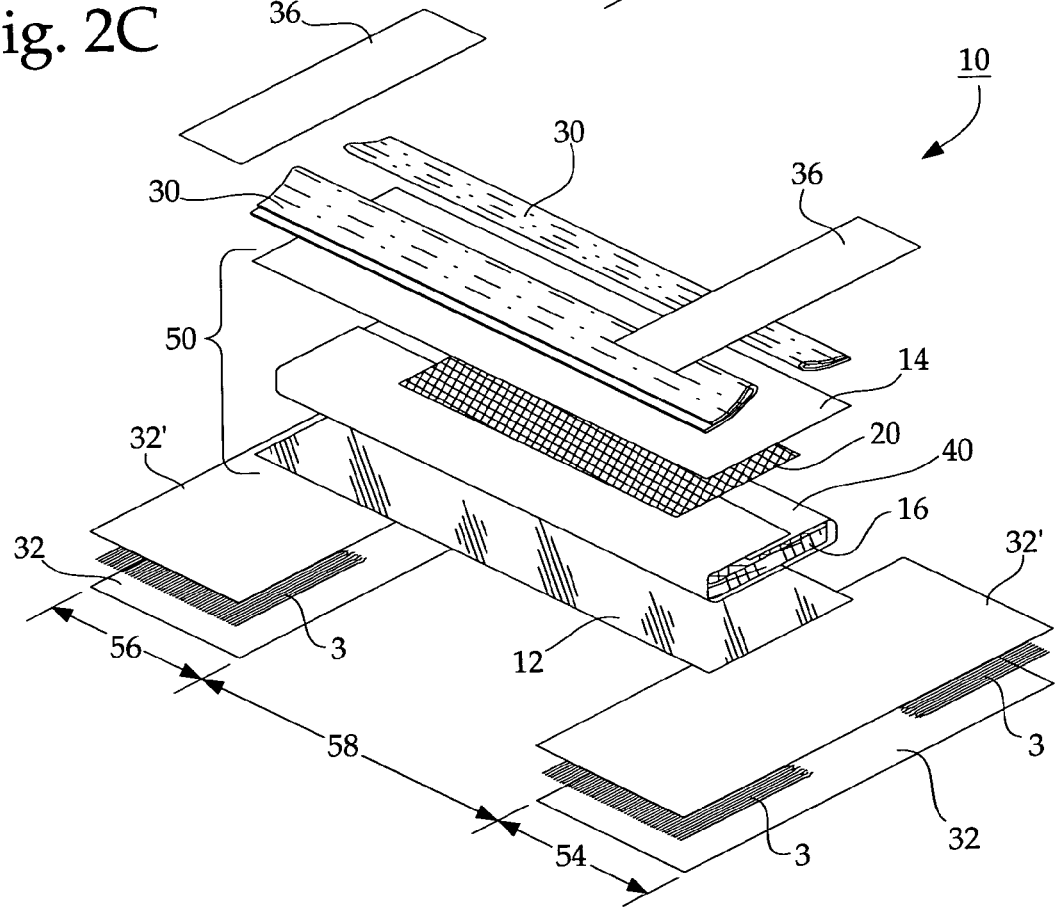
FIG. 2C is an exploded isometric view of still another embodiment of the present invention.

In a preferred embodiment of the invention, the topsheet 14 and chassis layer 34 comprise nonwoven materials and the backsheet 12 comprises a film material. The topsheet 14, backsheet 12 and chassis layer 34 may also be made, however, from any other suitable material. In various embodiments, one or more of the topsheet 14, backsheet 12 and chassis layer 34 may be selected to provide particular benefits to the garment 10. For example, they may be selected to provide a good tactile impression, or "hand," a comfortable fit, or gas permeability to improve the breathability of the garment 10. The visual aesthetics of the garment 10 also may optionally be changed or improved by adding graphics 21, as shown in FIGS. 1 and 2. The graphics may comprise any suitable images or designs, and may be applied by any suitable method, such as the methods disclosed in U.S. Pat. No. 6,558,499 to Pargass et al. and U.S. Pat. No. 5,826,543 to Ungpiyakul et al., which are incorporated herein by reference.

The absorbent core 16 may be made from any absorbent material or materials known in the art. In one embodiment of the invention, the absorbent core 16 comprises wood fibers or other fibers such as chemical wood pulp, fibrous absorbent gelling material, or any other suitable liquid absorbing material, such as commercially available fluff pulp or fluffed bleached kraft softwood pulp or fibrous absorbent gelling material. In another embodiment of the invention, the absorbent core 16 comprises a combination of a porous fibrous web and super absorbent particles. Absorbent cores are known in the art and are disclosed, for example, in U.S. Pat. No. 5,281,207 issued to Chmielewski et al., U.S. Pat. No. 4,610,678 issued to Weisman et. al., U.S. Pat. No. 5,137,537 issued to Herron et. al., and U.S. Pat. No. 5,147,345 issued to Young et. al., which are incorporated herein by reference in their entirety, and in a manner consistent with the present invention. In such an embodiment, the absorbent core 16 may be surrounded by a liquid pervious tissue over-wrap (such as tissue wrap 40 in FIG. 2C), or other material.

The absorbent core 16 generally is elongated along the longitudinal axis 100 of the garment, and may extend along either or both of the lateral and longitudinal axes 102, 100 to the outer perimeter of the garment. In the embodiment depicted in FIGS. 1 and 2A, the absorbent core 16 is substantially rectangular in shape, however, it may also have rounded ends or other shapes, such as an "I" shape or a "T" shape. The absorbent core 16 may also have channels, grooves or pockets, and may have a varying thickness.

The various parts of the garment 10 preferably are operatively associated with one another in such a manner that the garment will maintain its desired structure during use. The parts may be operatively associated with one another by a variety of methods known in the art, including, but not limited to: using adhesives such as hot melt adhesives and construction adhesives, chemical or solvent bonding, ultrasonic welding, stitching, heat bonding, autogenous bonding, or any other method of affixation known or hereafter discovered. U.S. Pat. No. 4,919,738 issued to Ball et. al. discloses a method of autogenous bonding, and its disclosure is herein incorporated by reference in its entirety in a manner consistent with the invention. All of the parts may be joined to each adjacent part, but some parts may not be joined to others. For example, the topsheet 14, backsheet 12 and core 16 may be directly attached to one another, or the topsheet 14 and backsheet 12 may be bonded to one another around their perimeter regions, thereby encasing and holding the absorbent core 16 in place without having to directly join the absorbent core 16 to any parts of the garment 10. As understood herein, the term "operatively associated" includes directly joining one part to another, indirectly joining parts together through one or more intermediary parts, whether those intermediary parts are described herein or not, joining parts in such a manner that unjoined parts are captured or held in their proper place, and any other suitable joining means that maintains the structural integrity of the garment 10 for the duration of its use.

In a preferred embodiment of the present invention depicted in FIGS. 1 and 2A, the garment 10 further comprises various mechanisms for improving the garment's ability to contain body exudates, such as standing leg gathers 30. Standing leg gathers 30 may be formed by incorporating a plurality of gather elastics 6 into folds in the topsheet 14 or into additional ribbons 38 that are attached to the garment near the leg holes 22. The gather elastics 6 cause the standing leg gathers 30 to rise above the interior surface of the garment 10, or wrap around the wearer's legs, thereby forming vertical curtains of material that help contain exudates. The ribbons 38 may be liquid pervious or liquid impervious, and more than one pair of opposing standing leg gathers 30 may be provided. The standing leg gathers 38 may be attached to the topsheet 14, backsheet 12, chassis layer 34 or any other suitable part of the garment, and may extend along the longitudinal axis 100 or lateral axis 102 or at an angle in between the axes to help block or impede the passage of fluids and other exudates. Additional elastics (not shown) may also be incorporated into the chassis layer 34, topsheet 14 or backsheet 12 adjacent the leg holes to form conventional (i.e., non-standing) leg gathers, as known in the art. Conventional gathers contract the garment 10 around the wearer's legs and body to prevent leakage. U.S. Pat. Nos. 3,860,003 and 4,081,301 issued to Buell, U.S. Pat. No. 4,695,278 issued to Lawson, U.S. Pat. No. 4,808,177 issued to Des Marais, U.S. Pat. No. 4,795,454 issued to Dragoo, and U.S. Pat. No. 4,938,755 issued to Foreman illustrate other embodiments of leg cuffs and gathers in absorbent garments, and the disclosures of these patents are hereby incorporated by reference in their entirety, and in a manner consistent with the present invention.

The core assembly 50 may comprise additional layers of material that may reduce rewet of the topsheet 14, reduce strikethrough times or otherwise improve the absorbency, dryness and other properties of the garment 10. For example, a transfer layer 20 comprising an apertured film or an air-bonded carded, bicomponent fiber nonwoven, having a basis weight of about 20 g/m$^2$ to about 100 g/m$^2$, and more preferably about 30 g/m$^2$ to about 60 g/m$^2$, and most preferably about 40 g/m$^2$ may be disposed between the topsheet 14 and the absorbent core 16. Such multiple layer absorbent cores are known in the art.

The core assembly 50 may be attached to the chassis layer 34 by any means known in the art, such as by ultrasonic bonding or by the use of lines of hot melt adhesive. The bond between the core assembly 50 and the chassis layer 34 may be reinforced by laterally-extending end strips 36 that are applied over the longitudinal ends of the core assembly 50 and bonded to the underlying structure of the garment 10. The end strips 36 may also hold the ends of the standing leg gathers 30 so that the standing leg gathers 30 face inwardly. Such end strips 36 preferably comprise a fluid pervious nonwoven material, but may be fluid impervious or a material other than a nonwoven material. Such materials are known in the art. The end strips 36 may also help prevent the longitudinal flow of exudates past the ends of the core assembly 50, particularly if the edges of the nonwoven strips overlying the core assembly 50 are left unbonded so that they form pockets to hold exudates. The end strips 36 may extend along the entire width of the garment 10 or along only a portion thereof.

In other embodiments, adjustment strips (not shown) may be disposed on and partially attached to the garment to provide for an adjustable fit. Absorbent garments often loosen during use for various reasons, such as inelastic stretching of the various components, changes in user size, and increased loading caused by the introduction of body exudates into the garment 10. The adjustment strips may be formed such that they may be releasably attached to the garment 10 to reduce the circumference of the waist encircling edge 4', and may comprise any fastening means known in the art or later discovered.

It is often desirable for an absorbent garment to contract around various parts of the wearer's body to provide improved comfort and exudate containment. In addition to the standing leg gathers 30 or conventional gathers, waist elastics 5 and stomach elastics 3 may be incorporated into the garment 10 to contract the garment 10 about the wearer's waist and stomach. Such elastics are typically stretched as they are joined to the garment 10 so that the contraction of the elastics causes the garment 10 to contract about the wearer. The elastics may also be applied in an unstretched state and then mechanically stretched to create an elasticized region in the garment (often called a zero-strain laminate). The elastics may also be applied in an inelastic state and then heat activated to cause them to be come elasticized. The elastics 3, 5, and 6 may be made from natural or synthetic rubber, elastomers, LYCRA™ elastomer (available from E.I. DuPont de Nemours and Company, a business having offices in Wilmington, Del.), polyurethane, heat shrinkable polymer ribbons, or any other suitable elastic material or composite. In a preferred embodiment, the stomach elastics 3 comprise a plurality of elastic strands or ribbons, and not an elastic film, in order to provide greater breathability.

In a preferred embodiment, the waist elastics 5 are located proximal to one or both longitudinal ends 4 of the chassis layer 34, and are thereby located along the waist encircling edge 4' of the fully assembled garment 10. In such an embodiment, the waist elastics 5 may be located on one side of the chassis layer 34, within a fold in the chassis layer 34 (as shown in FIG. 2A), or otherwise fixed in the proximity of the longitudinal ends 4. In a preferred embodiment, the garment 10 has three waist elastics 5, one of which has a 1100 decitex, and two of which have an 800 decitex. U.S. Pat. No. 4,515,595 issued to Kievit et. al. and U.S. Pat. No. 4,816,025 issued to Foreman illustrate other embodiments of elasticized waist features of absorbent garments, and are hereby incorporated by reference in their entirety Stomach elastics 3 may also be disposed in the garment 10 between the longitudinal ends 4 and the leg opening cutouts 22 to thereby be positioned across the wearer's stomach. It will be apparent to those of ordinary skill in the art that the term "stomach elastics," as used herein, also includes elastics that extend across the wearer's lower back, as shown in FIGS. 1 and 2A. The stomach elastics 3 may be attached directly to the chassis layer 34 but are preferably sandwiched between a pair of carrier layers 32, 32' to form elastic assemblies 52 that are attached to the chassis layer 34. The stomach elastics 3 may be located on the interior or exterior side of the chassis layer 34, and may be covered by additional layers of material. The carrier layers 32, 32' preferably comprise nonwoven materials, but may be made of any suitable material, and may be liquid pervious or liquid impervious. The carrier layers 32, 32' are preferably gas pervious to allow the garment 10 to "breathe."

In one embodiment, the stomach elastics 3 may extend across the entire width of the garment 10. In a preferred embodiment, however, shown in FIGS. 1 and 2A, the stomach elastics 3 extend across the lateral sides of the garment 10, but not across the portion of the garment 10 overlying the absorbent core 16. Such a preferred embodiment may provide improved fit and comfort and improve the garment's appearance. U.S. Pat. No. 5,449,353 issued to Watanabe et. al. and U.S. Pat. No. 5,749,865 issued to Yamamoto et al. illustrate other embodiments of elasticized waist features of absorbent garments, and are incorporated herein by reference in their entirety, and in a manner consistent with the present invention.

In the embodiment of FIG. 2A, the stomach elastics 3 form an elastic layer that is divided into first and second portions, with the first elastic layer portion located at a first end of the elastic assembly 60 and is attached to the chassis layers 32, 32' to form a first elasticized portion, and the other elastic layer portion located at a second end of the elastic assembly 62 and is attached to the chassis layers 32, 32' to form a second elasticized portion. A substantially inelastic region 64 is located between the first and second elasticized portions. Of course, heat-activated elastics or other elastics that are applied in a non-extended state may be used instead.

The inelastic region 64 preferably is formed, as described in more detail elsewhere herein, by extending full-length stomach elastics 3 across the entire width of the elastic assembly 52, gluing them at the ends but not in the middle, and severing the elastic assembly 52 in the middle to release the tension on that portion of the elastics. In this embodiment, there is a third elastic layer portion located in the substantially inelastic region 64 but not attached to the carrier layers 32, 32' in such a way to impart elasticity thereto.

When installed into the garment 10, the first end 60 of the elastic assembly 52 is positioned so that the first elasticized portion overlaps a first lateral side 66 of the waist region 54, and the second end 62 of the elastic assembly 52 is positioned so that the second elasticized portion overlaps a second lateral side 68 of the waist region 54. The substantially inelastic region 64 overlaps a central portion 70 of the waist region. In a preferred embodiment, the absorbent core 16 is located within the central portion 70 of the waist region, and thus the elasticity imparted by the elastic assembly 52 does not directly press against the core 16. Of course, some overlap between the stomach elastics 3 and the core 16 may result from manufacturing variations and may even be desirable to provide a smooth-looking transition to the core 16. Such variations are within the scope of the present invention.

The elastic assembly 52 of the present invention can be integrated into various different types of absorbent garment. For example, in FIG. 2A, the absorbent garment 10 is of the "training pant" or "pull-up" type, which uses an outer chassis layer 34 to form a pant-like main structure to which a separate absorbent core assembly 50 is attached. The elastic assembly 52 of the present invention can be conveniently integrated into such a garment 10 as explained elsewhere herein. The elastic assembly 52 can also be integrated into diaper-type garments in which the main structure is formed by the backsheet 12, topsheet 14, or both, as shown in FIG. 2B. In such an embodiment, the elastic assembly 52 can be positioned between the topsheet 14 and backsheet 12, as shown, or can be attached outside the backsheet 12 (to face outside the garment 10) or inside the topsheet 14 (to face inside the garment 10). As with the other garments described herein, the garment 10 of FIG. 2B may be joined along its seams 48 as shown in FIG. 1, or may be attached using fastener tabs (not shown) as known in the art. The elastic assembly 52 of the present invention also may be used alone or substantially alone to form the structure of the first and second waist regions 54, 56 of the garment 10. Such an embodiment is shown in FIG. 3B, in which the elastic assemblies 52 are attached to extend laterally from the longitudinal ends of the absorbent core assembly 50.

The elastic assembly 52 may be attached to the garment 10 using any suitable method, such as adhesive bonding or ultrasonic bonding, as will be appreciated by those of ordinary skill in the art. It has been discovered, however, that certain attachment methods are more favorable than others for producing a cloth-like absorbent garment, particularly when used in conjunction with certain constructions for the elastic assembly 52. Such methods are described elsewhere herein in more detail, particularly with reference to FIGS. 12 and 13.

Figure 3:
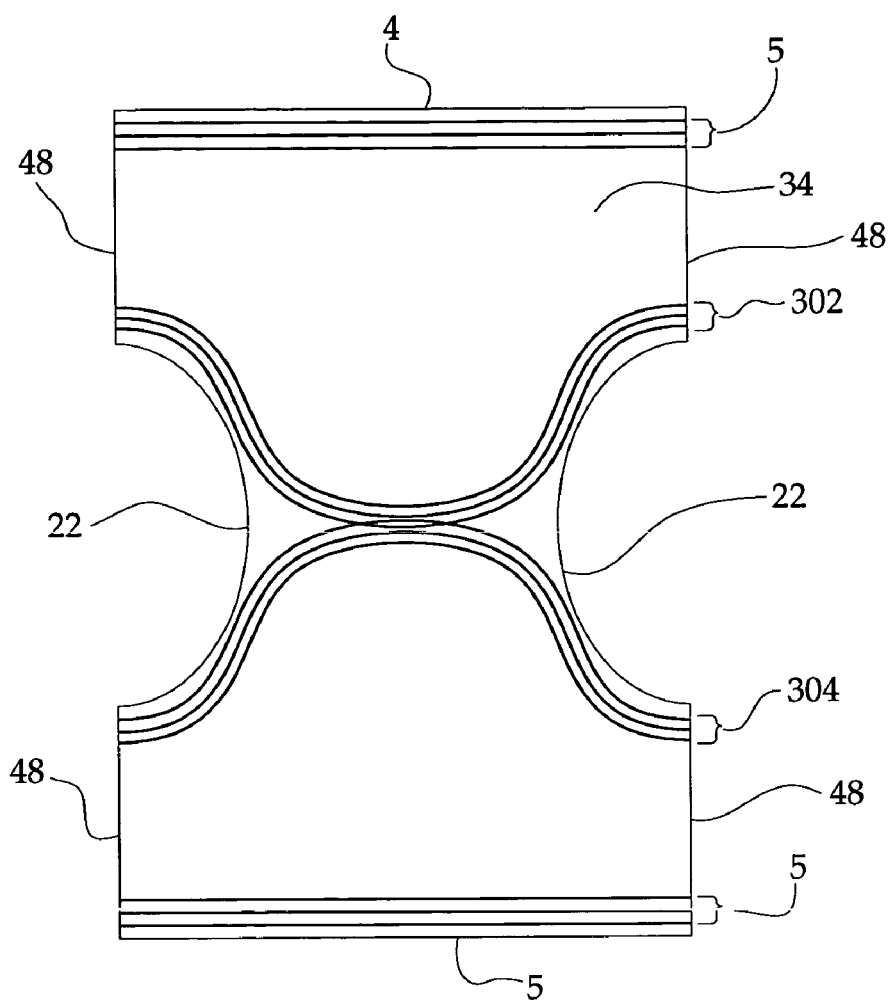
FIG. 3 is a schematic plan view of another garment according to another preferred embodiment of the invention.

In another preferred embodiment, such as the embodiment shown in FIG. 3, additional elastics may be applied to the garment 10 along the leg cutouts 22. In such an embodiment, a first set of elastics 302 may be attached around one half of a leg cutout 22, stretched across the middle of the garment 10, then attached around one half of the opposite leg cutout 22 in a sinusoidal pattern or other pattern, and a second set of elastics 304 may be applied in a similar manner to the other halves of the leg cutouts 22. The first and second sets of elastics 302, 304 may or may not overlap. Also, the first and second sets of elastics 302, 304 may also be severed between the leg cutouts 22 to improve the garment's appearance and fit. Such elastics are known in the art, and disclosed, for example, in U.S. Pat. No. 5,634,917 issued to Fujioka et al. and U.S. Pat. No. 5,836,931 issued to Toyoda et al., which are incorporated herein by reference in their entirety, and in a manner consistent with the present invention.

Figure 4:
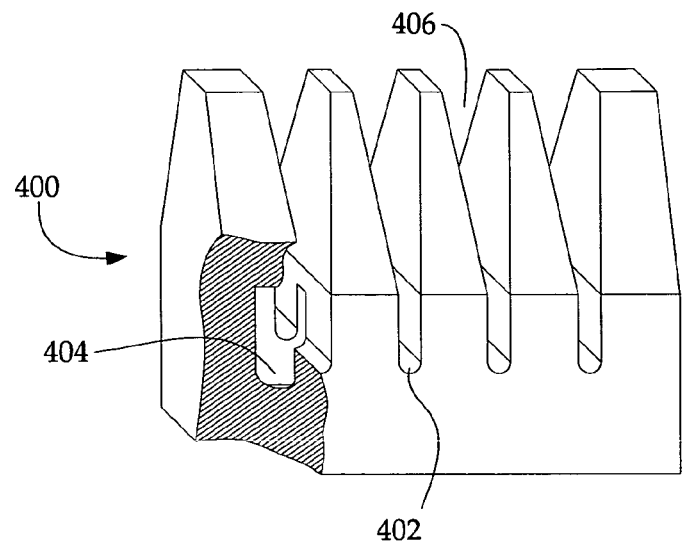
FIG. 4 is a partially cut away isometric view of an applicator comb according to a preferred embodiment of the invention.

The elastics 3, 5, 6 or any other elastics may be joined to the garment 10 by the use of a flexible adhesive such as HL 1486UZP, which is available from H. B. Fuller Company of St. Paul, Minn. In a preferred embodiment of the invention, the adhesive is applied to the elastics 3, 5, 6 by passing the elastics through a comb applicator 400, such as the one depicted in FIG. 4. The comb applicator 400 has one or more slots 402 through which individual elastic strands pass. Each slot is connected to an adhesive passage 404 through which adhesive is applied to the elastic strands. In operation, adhesive is heated (if necessary) and pumped or otherwise supplied or provided into the adhesive passages 404 to coat the elastic strands. The slots 402 shown in the Figures herein preferably have substantially parallel walls and a substantially semicircular bottom wall, but other shapes may be used, as will be apparent to those skilled in the art. Also in the embodiments depicted herein, the comb applicator 400 is depicted as having four slots arranged in a substantially straight line, however it should be readily apparent to those skilled in the art that fewer or more slots may be employed and the slots may be staggered relative to one another. The slots 402 may optionally be equipped with tapered entrances 406 to facilitate positioning the elastic strands within the slots 402.

Figure 5:
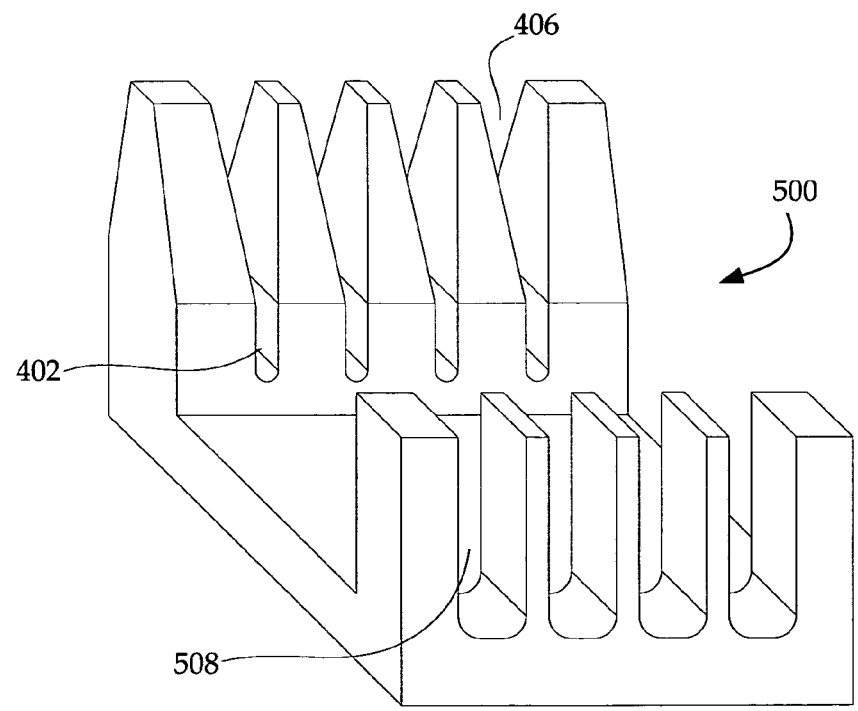
FIG. 5 is an isometric view of another applicator comb according to a preferred embodiment of the invention.

Referring to FIG. 5, the comb applicator may also optionally have a guide 508 on its entrance side that helps direct elastic strands into the slots 402 and reduce erratic movements of the elastic strands. Such a guide 508 may be particularly useful in an embodiment in which the comb applicator is moved laterally to guide the elastic strands through a variable path, such as the path of the leg elastics 302 and 304 in FIG. 3. A guide may also be positioned at the exit of the comb applicator 400.

The shape and size of the slots 402 is important for obtaining the desired adhesive coating pattern on the elastic strands. In a preferred embodiment, the adhesive fully coats the strands with adhesive around their entire periphery. The exact dimensions of each slot that may be used to obtain the desirable adhesive coating may depend on, for example, the size, e.g., the denier, decitex or diameter, of the elastic strand being coated, the degree of stretch of the elastic strand (to the extent that the stretch relates to the diameter of the strand), the length of the slots 402, the speed at which the elastic strand is moving, the viscosity and flow rate of the adhesive and the orientation of the comb applicator 400. One skilled in the art will be able to produce a suitable comb applicator 400 and adhesive application process without undue experimentation using the teachings provided herein.

Figure 6A:
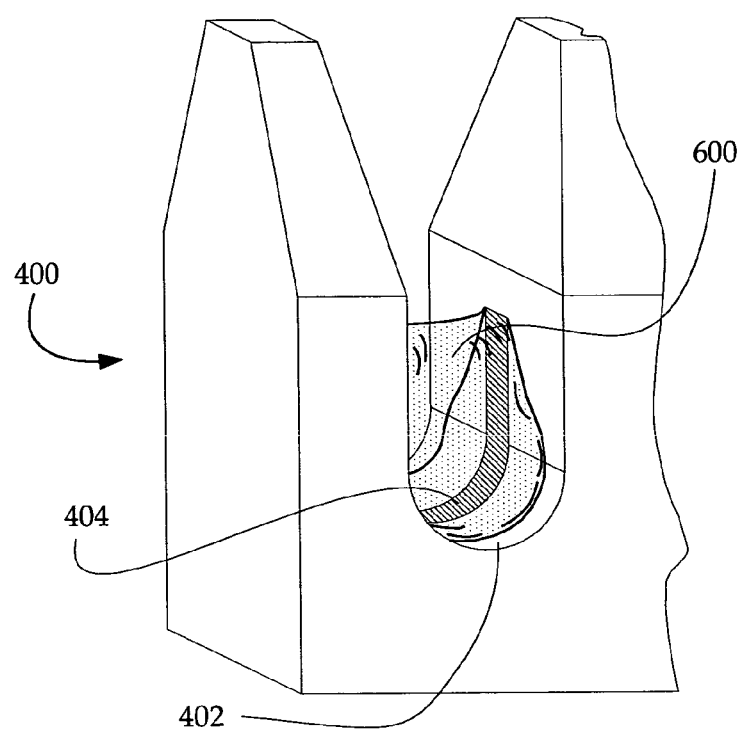
FIG. 6A is a partial isometric view of the applicator comb of FIG. 4, showing a slot filled with adhesive.
Figure 6B:
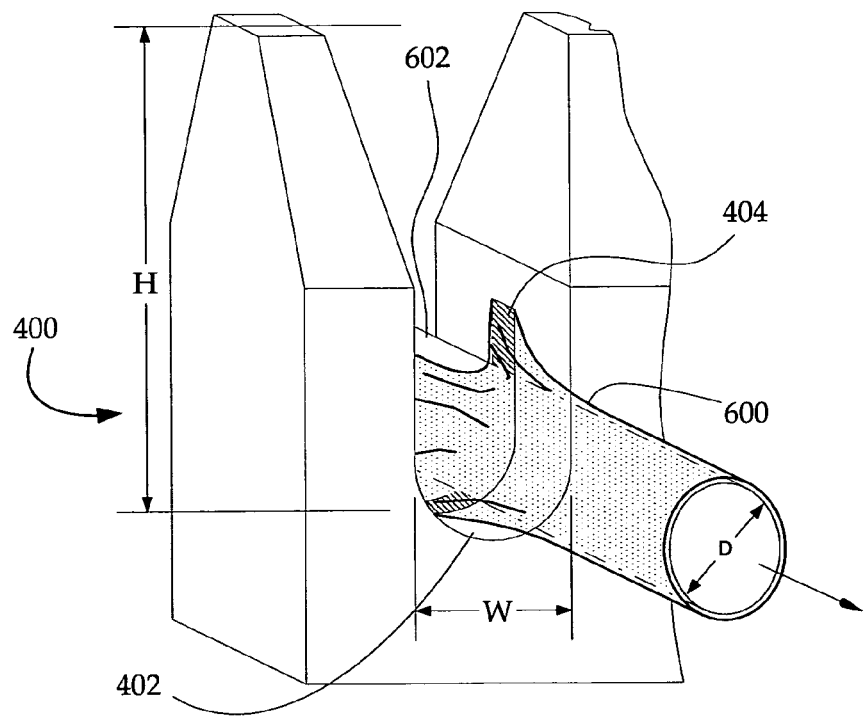
FIG. 6B is a partial isometric view of the applicator comb of FIG. 4, showing an elastic strand passing through the slot and being coated with adhesive.

The operation of the comb applicator may be better understood with reference to the exemplary depictions of an embodiment of the present invention shown in FIGS. 6A and 6B. In FIG. 6A, a comb applicator 400 is shown with a curtain of adhesive 600 emerging from the adhesive passage 404 to partially or wholly fill the slot 402. During a preferred mode of operation, shown in FIG. 6B, an elastic strand 602 is immersed in the adhesive 600 and drawn in the direction indicated by the arrow. The adhesive 600 coats the elastic strand 602 around its entire periphery as the elastic strand 602 is pulled through the comb applicator 400.

As noted before, a number of variables will affect the degree to which the preferred coating is obtained. If the slot is too wide (dimension W in FIG. 6B) relative to the strand's periphery, e.g., diameter (dimension D in FIG. 6B), then an excessive amount of adhesive may pass through the adhesive passage 404, leading to, for example, wasted adhesive, clogging in the slot 404 and undesirable adhesive accumulations on other parts of the machinery and the garment. In a preferred embodiment, the slots 402 have a width W of about 0.005 inches (in) to about 0.050 in, and more preferably, the slots 402 have a width W of about 0.010 in to about 0.030 in, and most preferably, the slots 402 have a width W of about 0.015 in. Larger slots 402 may also be used for larger diameter elastic strands 602.

The height (dimension H in FIG. 6B) of the slots 402 may also affect the degree to which the preferred coating is obtained. If the height H is too low, the elastic strands 602 may lift out of the supply of adhesive 600 due to vibrations or other disturbances and not receive the desired adhesive coating. If the adhesive passage 404 is too tall, excess adhesive may accumulate within the slot, degrading performance and requiring more frequent service. In a preferred embodiment, the adhesive passages 404 have a height H of about 0.050 in to about 0.105 in, and more preferably, the adhesive passages 404 have a height H of 0.065 in to about 0.090 in, and most preferably, the adhesive passages 404 have a height H of about 0.079 in.

While it has been found that elastic strands 602 having a denier of about 200 to about 2200 (i.e., a decitex of about 220 to about 2440), may be used with the above-described slots. It has also been found that elastic strands having a decitex of less than about 220 (200 denier) also may be used with the above-described slots with favorable results. Examples of the use of elastics in both ranges are described elsewhere herein.

Figure 11:
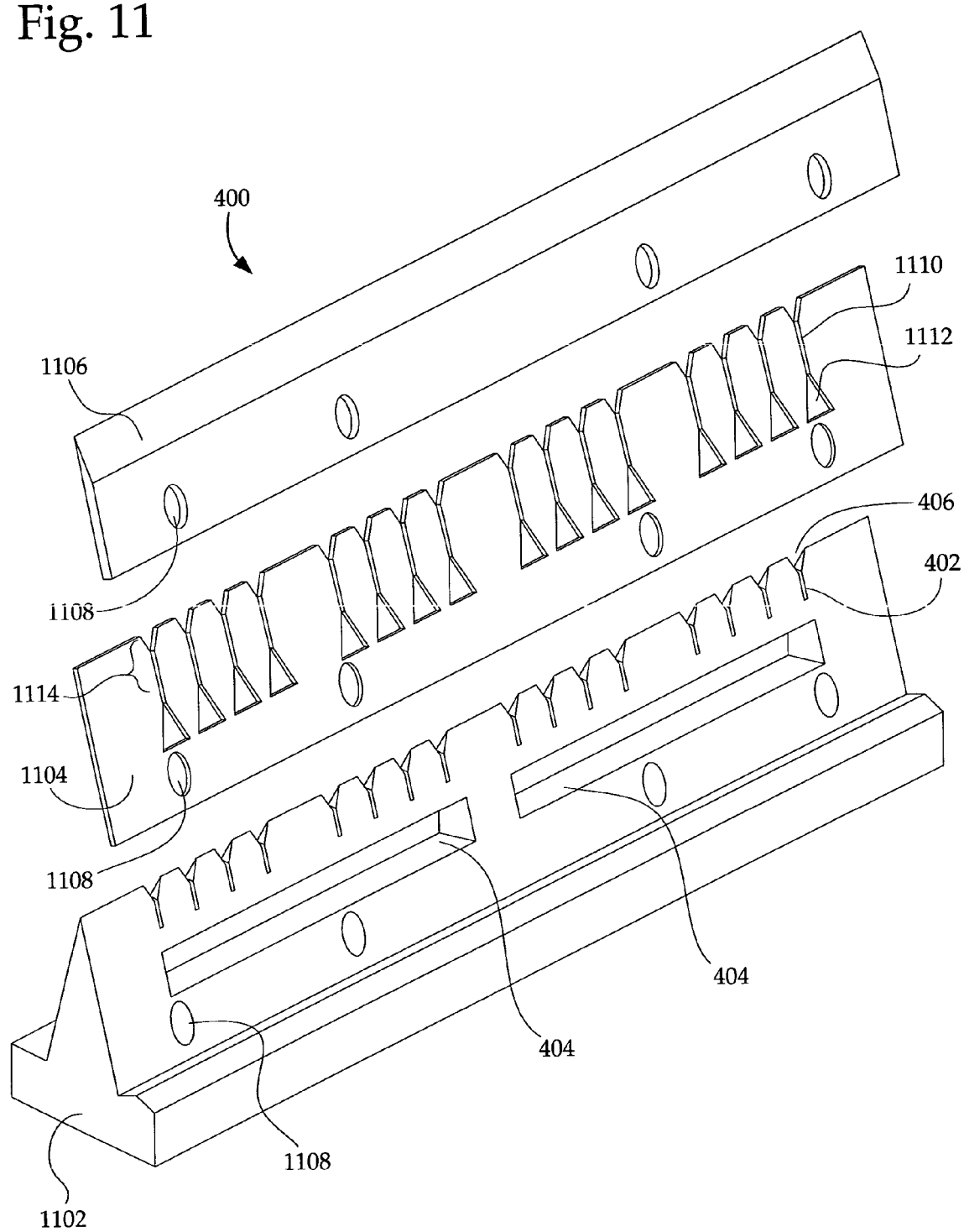
FIG. 11 is an exploded isometric view of a preferred embodiment of a comb applicator suitable for use with the present invention.

Referring now to FIG. 11, the design of the adhesive passage 404 may also influence the distribution of adhesive onto the elastic strands 602. For example, FIG. 11 depicts an exploded view of a preferred embodiment of a comb applicator 400 having sixteen slots 402. The comb applicator 400 comprises a base plate 1102 that is notched to form at least part of each of the slots 402 and their corresponding tapered entrances 406. The base plate 1102 also has two separate adhesive passages 404 within it, which may be fed by a common source or different sources. In use, a feed shim 1104 is sandwiched between the base plate 1102 and a clamping strip 1106. The base plate 1102, feed shim 1104 and clamping strip 1106 may be held together using screws that pass through screw holes 1108, clamps, or any other suitable fastening device.

The feed shim 1104 has a feed port 1110 and feed gallery 1112 corresponding to each slot 402. In operation, adhesive passes from the adhesive passages 404, into the feed galleries 1112, and through the feed ports 1110. Each feed port 1110 may terminate at the base of its corresponding slot 402, or may extend upward to form part of the slot 402. For example, as shown in FIG. 11, the upper portion 1114 of each feed port 1110 is shaped to have the same profile as the corresponding slot 402, and when the comb applicator 400 is fully assembled the upper portions 1114 of the feed ports 1110 form part of the slots 402. The clamping strip 1106 seals the assembly so that adhesive may only pass out through the feed ports 1110.

In the embodiment of FIG. 11, the amount of adhesive passing to each slot 402 may be regulated by changing the thickness of the feed shim 1104, with a thicker feed shim 1104 supplying more adhesive than a thin feed shim 1104. The relative amount of adhesive flow between each of the slots 402 may be regulated by making the feed ports 1110 supplying certain slots 402 narrower or wider than those supplying other slots 402. Such a relative difference in the amount of adhesive flow may be desirable to provide a greater amount of adhesive to slots 402 being used to coat larger elastic strands 602. In addition, it may be desirable to make some feed ports 1110 wider than others to equalize uneven adhesive flow caused by some slots being located farther from the adhesive source than others. The design of adhesive passages 404 and feed ports 1110 to obtain these and other goals is generally known in the art, and a skilled artisan will be able to design appropriate adhesive passage 404 and feed port 1110 systems without undue experimentation based on the teachings provided herein.

The length of the slot 402 may also affect the performance of the present invention. Longer slots 402 may prevent adhesive from being sprayed out of the slots and onto the assembly or the surrounding machinery. Longer slots may also allow more adhesive 600 to be pooled around the elastic strands 602 to provide more consistent coating. In one embodiment, the slots 402 have a length of about 0.010 in to about 0.065 in, and more preferably a length of about 0.022 in to about 0.052 in, and most preferably a length of about 0.037 in.

The diameter D of the elastic strand 602 may be reduced by providing the strand 602 with additional stretch. In some cases, the elastic strand 602 may require a minimum amount of stretching in order to pass through the slot 402 and obtain the desired adhesive coating. In one embodiment, the elastic strands 602 are stretched to about 250% to about 400% of their original length when they are passed through the slots 402, and more preferably, the elastic strands 602 are stretched to about 275% to about 375% of their original length when they are passed through the slots 402, and most preferably, the elastic strands 602 are stretched to about 300% to about 350% of their unstretched length when they are passed through the slots 402.

The elastic strands 602 may also have a non-circular shape, such as an elliptical or rectilinear or other shape, that may have one or more long axes and one or more short axes. In such a case, it may be desirable to ensure that the aspect ratio (as measured by the long axis size divided by the short axis size) is not so great as to inhibit the ideal coating of the elastic. In a preferred embodiment, the aspect ratio is between about 3:1 to about 1:1. In a more preferred embodiment, the aspect ratio is about 2:1 to about 1:1.

The speed at which the elastic strand 602 is drawn through the slot 402 may also affect the adhesive coating process. If the strands 602 are moving too fast, then they may receive an insufficient amount of adhesive coating, and may spray adhesive outside the comb applicator 400, causing undesirable adhesive build-up on other parts of the machine or the assembly. If the strands are moving too slow, then they may receive too much adhesive, and unapplied adhesive may flow out of the comb applicator 400 and build up on the surrounding machinery and assembly.

The speed of the elastic strands 602 should be matched to the viscosity and flow rate of the adhesive 600. Lower viscosity adhesives may tend to drain out of the comb applicator 400 or be sprayed by the elastic strand 602 to build up on other parts of the machinery or the assembly. Higher viscosity adhesives may resist full application around the periphery of the elastic strands 602 and may tend to harden and clog in the slots 402. The viscosity of the adhesive 600 may generally be varied by heating or cooling the adhesive 600 or by providing a different adhesive 600. In a preferred embodiment, the adhesive is H.B. Fuller Company's HL 1486UZP which is supplied in the comb applicator 400 at a temperature of about 250 degrees Fahrenheit to about 350 degrees Fahrenheit, or more preferably at about 275 degrees Fahrenheit to about 325 degrees Fahrenheit, and most preferably at about 290 degrees Fahrenheit to about 310 degrees Fahrenheit.

The flow rate of the adhesive may also impact the adhesive application process. The desired flow rate may be calculated by determining the volume of adhesive 600 that is desired to be applied to a given length of the elastic strand 602, then scaling this value to match the speed of the elastic strand 602. Once this value is determined, other variables, such as the viscosity of the adhesive 600, the temperature at which the adhesive is supplied, and so on, may be varied to obtain an ideal adhesive coating.

Figure 7:
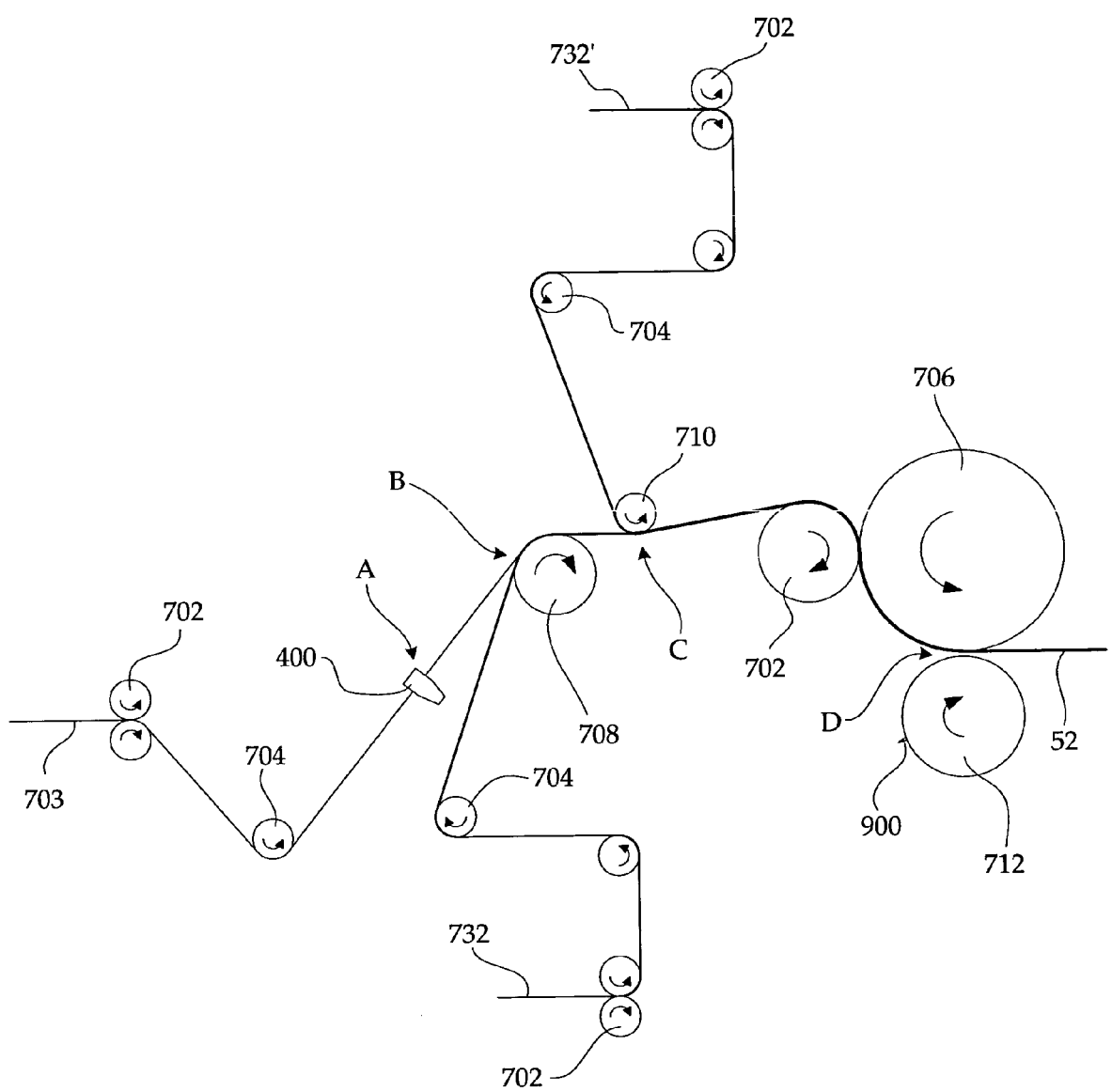
FIG. 7 is a diagram of a manufacturing line according to a preferred embodiment of the invention.

It has been found that the comb applicator 400 of the present invention may be operated in any orientation, with or without adjustment to the other variables, but that some orientations may provide better adhesive coating than others. In a preferred embodiment of the invention, the comb applicator 400 is angled downwardly (i.e., with the open ends of the slots 402 pointing downwardly, as shown in FIG. 7) at an angle of about 5 degrees to about 85 degrees, and more preferably at about 30 degrees to about 60 degrees, and most preferably at about 45 degrees. Similar upward orientations are also desirable in another preferred embodiment. Excess adhesive, if any, may be collected on a drip pan (not shown) located beneath the comb applicator, and such collection may be facilitated by orienting the comb applicator at a downward angle.

A suitable comb applicator that may be used with the present invention is supplied by Suntool of Osaka, Japan.

It may be desirable to apply adhesive to the elastics 3, 5, 6 only along a portion of their lengths, so that the portions of the elastics 3, 5, 6 do not receive any adhesive coating and do not adhere to the garment. In one embodiment of the invention this may be accomplished by intermittently cutting off the supply of adhesive 600 in the adhesive passages 404. In one preferred embodiment, a pump that supplies adhesive to the comb applicator may be equipped with a backflow device that draws adhesive out of the slots 402 and into the adhesive passages 404 so that the adhesive no longer contacts elastics 3, 5, 6. Such a backflow device may allow for relatively precise cutoff of the adhesive application, providing easier use and reducing inadvertent adhesive application. Other methods of cutting off the adhesive supply to the elastic strands include simply cutting off the flow of adhesive 600 or momentarily lifting the elastic strands out of the slots by using, for example, a reciprocating guide or a rotating cam with a lifting lobe. Other methods of momentarily ceasing the application of adhesive to the strands will be evident to those skilled in the art in light of the teachings herein.

The adhesive coating of the present invention provides significant benefits over the currently known adhesive coating techniques. The adhesive coating techniques of the prior art used multiple pressurized spray guns to eject adhesive onto the elastic strands, leading to excessive adhesive usage and undesirable overspray. Such techniques also do not fully and uniformly coat the elastic strands, thereby providing a weaker bond with the underlying sheet material to which the elastic strands are attached. Using the present invention, the elastic strands are substantially fully and uniformly coated with adhesive following immersion in the adhesive-filled comb applicators 400, thereby providing a stronger and therefore superior finished garment. Furthermore, there is no adhesive overspray onto the outer nonwoven material or the assembly machine, and the resulting garment is softer due to the absence of hard spots from hardened oversprayed adhesive on the various garment materials.

Referring now to FIG. 7, a preferred method for applying elastics to a garment is described. In a preferred embodiment depicted in FIG. 7, continuous supplies of first and second carrier layer material 732, 732' are supplied. A continuous supply of one or more elastic strands 703, which may be supplied by a single spool or a number of spools, is supplied to be fed between the first and second supplies of carrier layer material 732, 732'. The supplies of carrier layer material and elastic strands 732, 732', 703 may be held by pinch rollers 702 and tensioned by adjustable tensioning rollers 704 to obtain the desired position, speed and tension in each supply. A drive roller 706 may be used in conjunction with a pinch roller 702 to pull the supplies 703, 732, 732' through the machinery. The drive roller 706, like the other rollers, may serve other functions, such as to simultaneously serve as an anvil roller against which a knife 900 presses to cut all or part of the supplies of elastic strands 703 and supplies of carrier layer material 732, 732' as described below.

At location A, a comb applicator 400 applies adhesive to the supply of elastic strands 703, as described above. Using the present invention, the comb applicator 400 may be located near one or both of the supplies of carrier layer material 732, 732' without any adhesive being sprayed onto those materials. At location B, a first side of the supply of elastic strands 703 contacts the first supply of carrier layer material 732 as the two supplies are drawn across a first guide roller 708. At location C, the second supply of carrier layer material 732' is pressed against the second side of the supply of elastic strands 703 by a second guide roller 710, which may be adjustable to apply the second supply of carrier layer material 732' with more or less pressure. The second guide roller 710 also may operate in conjunction with an anvil roller (not shown) to firmly press the material together. After location C, the now complete elasticized laminate structure 52 may be conveyed to other parts of the assembly line to be processed into standing leg gather assemblies, waist elastic assemblies, stomach elastic assemblies or other elastic assemblies that are incorporated into an absorbent garment. Such further processing is generally known by those skilled in the art. It should also be apparent to one skilled in the art that the above described steps may be transposed or altered in a number of ways to achieve the same end result, for example, the supply of elastic strands 703 may be applied to the second supply of carrier layer material 732' before being applied to the first supply of carrier layer material 732, or other devices may be used to tension, stretch, position, and drive the various material supplies. Such variations are within the scope of this invention.

In another embodiment of the invention, a comb applicator 400 may be used to supply adhesive to a supply of one or more elastic strands that are placed on a single supply of material that is folded over on itself to form an elasticized ribbon, such as those often used to make standing leg gathers 30, or form an elasticized edge of a sheet, such as to form elasticized waist edges or leg cutouts.

In another preferred embodiment, a comb applicator 400 is used to incorporate elastic strands into a stomach elastic assembly 52 comprising first and second carrier layers 32, 32' having one or more stomach elastics 3. The stomach elastic assemblies 52 may then be applied to one or both longitudinal ends 4 of the chassis layer 34 in the garment's first and second waist regions 54, 56. The stomach elastics 3 may extend across the entire width of the garment 10, or they may extend only partially across the garment's width. Furthermore, it may also be desirable to provide the first and second waist regions 54, 56 with stomach elastic assemblies 52 having different properties to improve aesthetics, comfort and leakage resistance. For example, the width, number of elastics, overall elasticity, location of the elastics, and so on may vary between the first and second waist regions 54, 56. Also, one waist region may have full-length elastics while the other has partial-length elastics, and one waist region may not have any stomach elastic assembly at all.

It has been found that to improve the garment's fit and aesthetic appeal it is desirable to provide stomach elastics 3 only along either side of the garment 10, and not across the middle of the garment 10 where the absorbent core 16 is located. One method for producing such a preferred embodiment is to use stomach elastic assemblies 52 that are only elasticized in those regions overlaying the sides of the garment, as shown in FIG. 2A. Such a stomach elastic assembly 52 may be easily produced using the present invention, and such a process is described herein with reference to FIGS. 7–10.

In order to produce a stomach elastic assembly 52 having discontinuous elastics, the stomach elastics 3 may be discretely coated along portions of their length so that they adhere to the first and second carrier layers 32, 32' in glued zones G, but do not adhere to the carrier layers 32, 32' in unglued zones U, as indicated in FIG. 8. The stomach elastics 3 are then severed in each unglued zone U by a notched knife 900 attached to a cutting drum 712, such as is shown in FIG. 9. The notched knife 900 forms cuts 800 in only those portions of the carrier layers 32, 32' that have stomach elastics 3 located therebetween, so that the carrier layers 32, 32' still continue along the assembly line as continuous supplies of material that are joined to one another by the adhesive-coated stomach elastics 3. The cut ends of the stomach elastics 3 snap back out of the unglued zone U, thereby providing elastication in the glued zones G, but not in the unglued zones U. Such a process may take place immediately after the stomach elastic assembly 52 is formed, such as at location D of FIG. 7, or at any other suitable location.

Figures 8A, 8B, 8C:
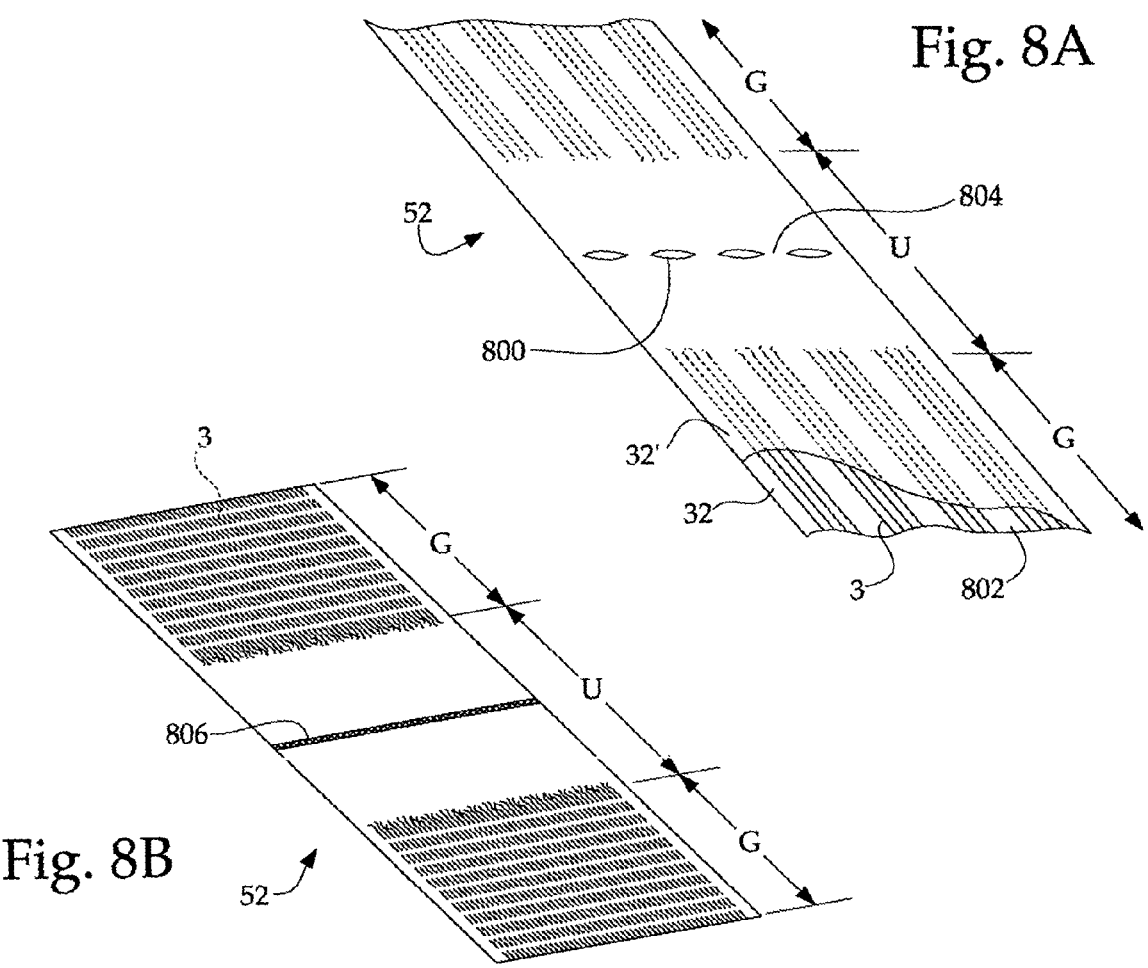
FIG. 8A is a partially cut away view of a portion of stomach elastic assembly manufactured according to a preferred embodiment of the present invention.
FIG. 8B is an isometric view of a portion of stomach elastic assembly manufactured according to another preferred embodiment of the present invention.
FIG. 8C is an isometric view of a portion of stomach elastic assembly manufactured according to still another preferred embodiment of the present invention.
Figure 9:
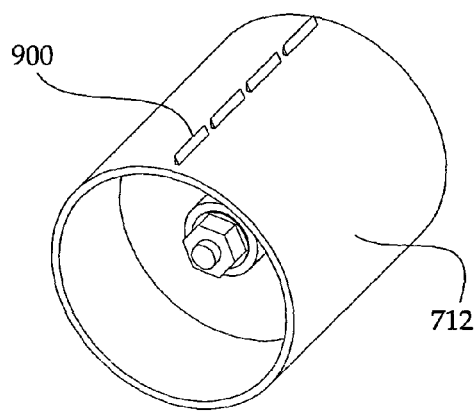
FIG. 9 is an isometric view of a cutting drum that may be used to fabricate a stomach elastic assembly as shown in FIG. 8A.
Figure 14:
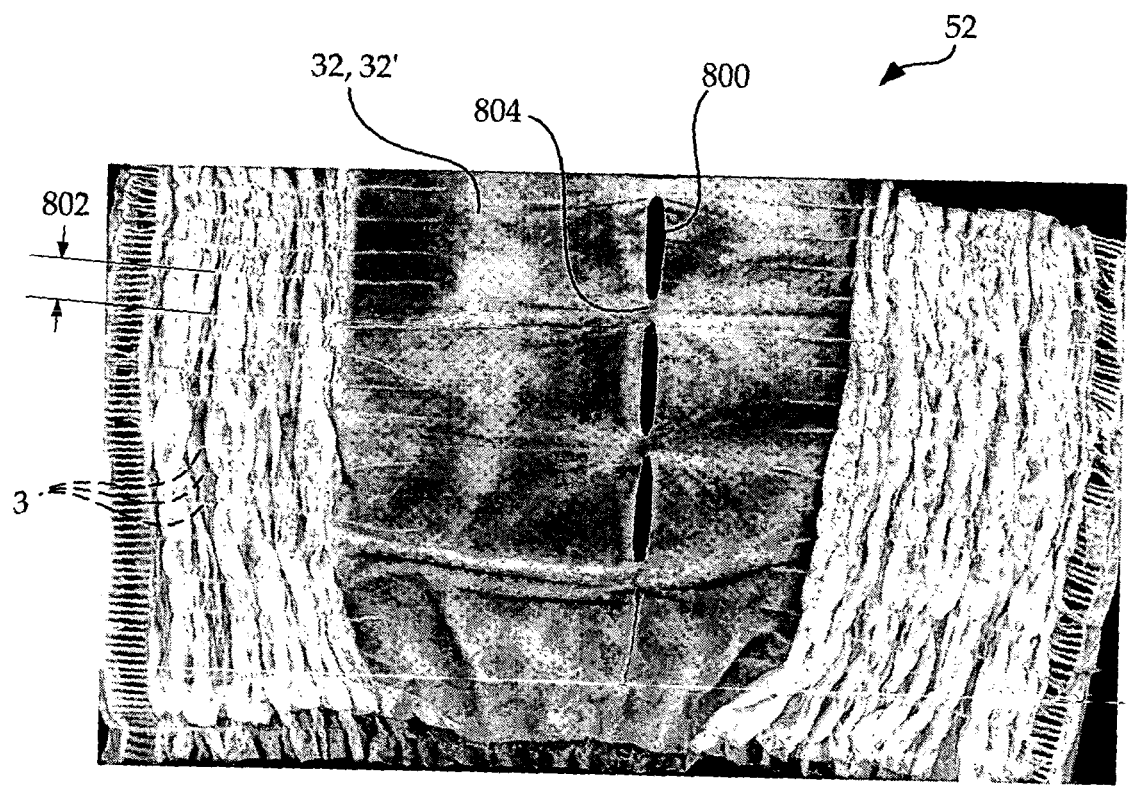
FIG. 14 is a photograph of a prior art elastic assembly.

In the embodiment of FIG. 8A (and FIG. 14), the stomach elastics 3 are separated into spaced-apart groups of elastics. This arrangement provides the benefit that the notched knife 900 only has to cut the elastic assembly 52 in those regions containing the elastics 3, and not in the spaces 802 between the elastics 3. The uncut portions 804 between the knife cuts 800 provide the elastic assembly 52 with strength sufficient to resist the tension applied during the manufacturing process. In FIG. 8A there are four groups of four stomach elastics 3, but other variations can be used.

In has been discovered, as described elsewhere herein, that certain beneficial properties may be obtained by an elastic assembly 52 with a relatively high number of relatively small stomach elastics 3, and in such an embodiment, the stomach elastics 3 may be very closely spaced. In such a case, the stomach elastics 3 may still be provided with spaces 802 between groups of elastics so that a notched knife 900 can be used to sever them, as just described.

Although the method of spacing and severing the stomach elastics 3 described with reference to FIG. 8A is effective, it has been found that it is more desirable to remove the spaces 802 between the groups of elastics to provide a more consistent look and feel to the garment to which the elastic assembly 52 is applied. It has been discovered that the need to provide spaces between the sets of elastics can be omitted by using certain methods to cut the stomach elastics 3.

In the first method, the elastics are severed by using an ultrasonic, heat or mechanical bonder to pinch the elastic assembly 52 and bond the carrier layers 32, 32' to one another, and simultaneously sever the stomach elastics 3 between the carrier layers 32, 32'. It is also anticipated that the elastics may be severed by using a heat welding process. Such an embodiment is shown in FIG. 8B, with the ultrasonic bond being designated by reference numeral 806. In FIG. 8B, the carrier layers 32, 32' are bonded with the elastics 3 therebetween in glued zone G and unglued zones U as described with reference to FIG. 8A, but the stomach elastics 3 are not separated by relatively large spaces 802 into separate groups. The proper selection of ultrasonic bonding frequency and force may depend on the materials being used and the size of the elastics, and can be determined by routine experimentation. Furthermore, the ultrasonic bond 806 can be just light enough to sever the elastics 3, and need not be strong enough to firmly affix the carrier layers 32, 32' to one another. Such a severing method effectively cuts the elastics 3 without compromising the structural integrity of the elastic assembly 52 and its ability to resist web tension applied to it during the manufacturing process.

The second method of severing the stomach elastics 3 when they are closely spaced together, while still maintaining the tensile strength of the elastic assembly 52, is shown in FIG. 8C. In FIG. 8C, the carrier layers 32, 32' and elastics are assembled as described with reference to FIG. 8B. In this embodiment, the stomach elastics 3 are severed by using a two-dimensional pattern of cuts 808, rather than the one-dimensional line of cuts 800 that is provided with the method of FIG. 8A. The two-dimensional pattern of cuts 808 can be created by using a cutting drum 712 similar to that shown in FIG. 9, but with a series of notched knives 900 rather than a single knife. In this case, the notches of successive knives would be offset relative to one another along the centerline of the drum to which they are attached to create the desired pattern. Preferably, the cutting drum 716 is heated so that the notched knives 900 heat bond the carrier layers 32, 32' together at the cuts, which helps maintain the strength of the elastic assembly 52 and helps retain the chopped remnants (see reference numeral 810 in FIG. 12) of the stomach elastics 3 within the garment 10. Of course, other methods can also be used to make the two-dimensional pattern of cuts 808. For example, a plate having the desired knife pattern can be pressed against the elastic assembly 52 to cut the elastics 3, or lasers or hydraulic cutting knives may be used.

One problem encountered with using a single notched knife, as in FIG. 8A, is that the stomach elastics 3 sometimes vary from their desired position when being fixed between the carrier layers 32, 32', causing the them to be aligned with the notch of the notched knife 900, rather than the cutting edge. In such a case, the elastic is not severed by the knife 900 and remains uncut in the final product. It has been found that using ultrasonic cutting, as in FIG. 8B, or a pattern of cuts 808, as in FIG. 8C, is effective at cutting all of the elastics and overcoming the deficiencies of the previous cutting methods. In the case of the ultrasonic cutting process, the ultrasonic horn and anvil can extend continuously across the width of the elastic assembly 52 so that the cutting process occurs regardless of where the stomach elastics 3 are. In the case of the pattern of cuts 808, stomach elastics 3 that are out of position for one knife will be severed by the consecutive knives of the two-dimensional pattern.

It has also been found that in cases where a knife is used to cut the stomach elastics 3, the notched knife 900 does not necessarily have to fully sever the stomach elastics 3 and the carrier layers 32, 32', and may instead simply press against the layers 32, 32' with enough force to damage the stomach elastics 3 by crushing them, thereby causing them to separate.

Figure 10:
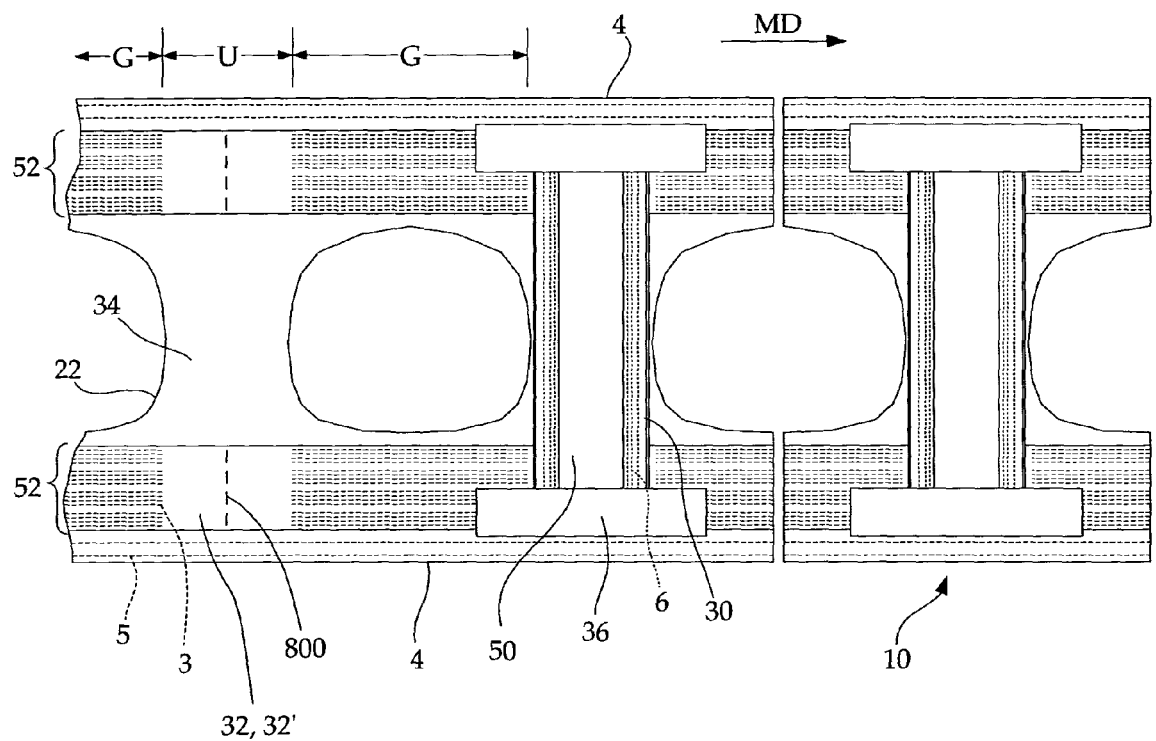
FIG. 10 is plan view of some of the manufacturing steps employed to manufacture the garment of FIG. 1.

Referring now to FIG. 10, stomach elastic assemblies 52 may be attached proximal to each longitudinal end 4 of the chassis layer 34, as it moves in the machine direction (indicated by the arrow MD). Each stomach elastic assembly 52 is positioned such that the unglued (inelastic) zones U overlap the part of the chassis layer 34 to which the core assembly 50 will be attached, and the glued (elasticized) zones G overlap the portions of the chassis layer 34 that will eventually form the sides of the garment. The core assembly 50, which may comprise the topsheet 14, backsheet 12, absorbent core 16, transfer layer 20 and standing leg gathers 30, may then be positioned on the chassis layer 34 between the leg cutouts 22 (naturally, the leg cutouts 22 may be made after positioning the core assembly 50). The ends of the core assembly then may be secured to the garment by overlapping them with discrete end strips 36, as shown, or with continuous end strips that extend along the entire width of the garment 10. Embodiments of the present invention may also be used to apply other elastics to an absorbent garment, such as waist elastics 5, and gather elastics 6. Once the assembly is complete, discrete absorbent garments 10 may be severed from the assembly, or the assembly may be folded and bonded to form a continuous supply of pant-like garments which is then severed into discrete garments 10. Those skilled in the art will understand that other steps may be employed to fabricate a complete absorbent garment, and one or more of the preceding steps may be rearranged, omitted, substituted or modified.

Such an embodiment is particularly desirable because it allows the elastics to be located in discrete areas, rather than continuously along the entire garment width. By maintaining the first and second carrier layers 32, 32' as a continuous supply of material, this method does not require the use of complex manufacturing techniques that are normally required to place discrete elasticized parts into a garment. Of course, it may be desirable to provide elastication completely across the stomach region, in which case the stomach elastics 3 may be adhered along the entire width of the garment and not severed.

Figure 12:
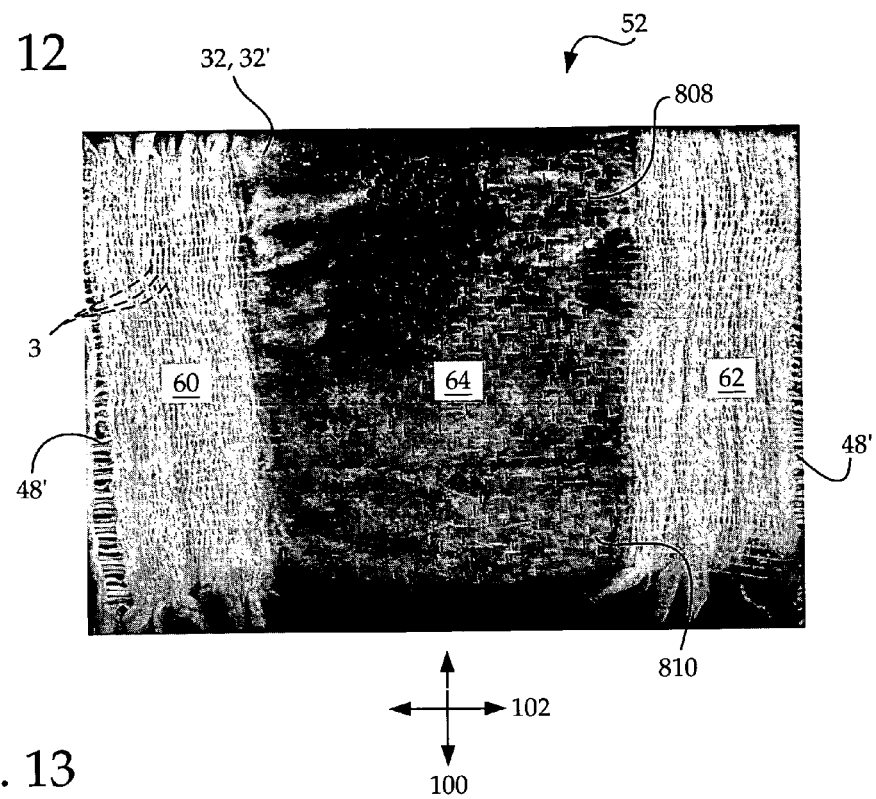
FIG. 12 is a photograph of an elastic assembly of a preferred embodiment of the present invention.

Referring now to FIG. 12, it has been discovered that the present invention can be used to provide an elastic assembly 52 that has improved aesthetics, comfort and leakage resistance as compared to conventional elastic strand laminate structures. Furthermore, the elastic assembly of the present invention provides breathability superior to that of laminates constructed using elastic films. Still further, the elastic assembly 52 of the present invention can be integrated into absorbent garments to provide a cloth-like garment having greater performance and consumer appeal. In general terms, the elastic assembly 52 uses a high number of closely-spaced low-weight (i.e., low denier/decitex) stomach elastics 3 that are sandwiched between two carrier layers 32, 32' to provide even distribution of forces around the wearer's body. In addition, the elastic assembly 52 is held together essentially only by a coating of adhesive that is applied to the elastics 3, thus greatly reducing the plywood effect that is prevalent in prior art garments.

The elastic assembly 52 of FIG. 12 was removed from one waist portion of the garment into which it was installed, and the remnants of the garment's side seams 48' are partially visible in FIG. 12. For clarity, the elastic assembly 52 is shown as it appears relative to the longitudinal and lateral axes 100, 102 of the garment 10 to which it would be attached. As used herein, the "length" of the absorbent assembly 52 is measured as it extends along the lateral axis 102 (i.e., the width) of the garment, while the "width" of the absorbent assembly 52 is measured along the longitudinal axis 100 (i.e., the length) of the garment.

Although the elastic assembly 52 of FIG. 12 is shown having two elasticized regions at its ends 60, 62 (shown elastically contracted) and a substantially inelastic region 64 between the elasticized regions, it will be understood that the entire elastic assembly 52 may be elasticized, or other patterns of elasticized and non-elasticized regions may be employed. It is also envisioned that the elastic assembly 52 can have an inelastic region 64 that does not extend through the entire width (in direction 102) of the elastic assembly 52. Although the embodiment of FIG. 12 is shown with the inelastic region 64 being formed by cutting the stomach elastics 3 with a pattern of cuts 808, other methods of severing the stomach elastics 3 also may be used, such as using a single line of cuts (as shown in FIG. 8A) or using an ultrasonic or heat bond between the carrier layers 32, 32' (as shown in FIG. 8B). It will be seen that the chopped remnants 810 of the stomach elastics 3, which are elastically contracted and do not add any substantial amount of elastication to the inelastic region 64, are visible in the inelastic region 64.

As used herein, an elastic strand's "strength" or "weight" refers to the elastic contracting force per unit length of extension (i.e., grams/centimeter) of each elastic strand (i.e., the elastic's spring constant). It will be understood by those of ordinary skill in the art that the strength of an elastic depends on the elastic material, the cross-sectional area of the elastic and the length of the elastic. When small elastic fibers having relatively small cross-sectional areas are used, it is often more convenient to refer to the fiber's decitex (weight of fiber in grams per 10,000 meters of fiber) or denier (g/9,000 m) to describe the cross-sectional size of the fibers. When elastic strands are present in a group, the "density" of the elastic strands refers to the spacing of the elastics (i.e. # of elastics/cm), with greater densities equating to more elastics per centimeter. The "overall contracting force" of an elastic assembly 52 or garment 10 refers to the combined contracting force of all of the elastics located in the particular region in question of the assembly or garment. It will be appreciated that the overall contracting force of and elastic assembly 52 will be a function, inter alia, of the strength of the individual elastics and the density of the elastics.

It has been discovered that baby training pants are particularly functional when they are designed to have side panels that allow about 350% elongation, and that have a total contracting force of about 3,500 grams to about 4,100 grams, and most preferably about 3,850 grams, at full extension. The "total contracting force" is the amount of force required to extend the garment to its fully-extended state. The fully-extended state of the garment is generally the length of the nonwoven substrates as they were before having the elastics installed into them. The total amount of extension of the garment is typically related to the amount that the elastics are extended before being installed into the garment, because this will determine how much the garment contracts when the elastics are allowed to relax, as will be understood by those of ordinary skill in the art. The total contracting force is typically measured by laying the garment flat, holding the garment at each side edge, and extending it by applying a tensile force until the elastics are extended to the same degree that they were extended when installed, or until the garment begins to plastically deform or tear. This measurement may be taken with the garment bi-folded at the core and attached at its side seams (as shown in FIG. 1) by gripping and pulling the side seams, or it may be taken with the garment unfolded and the side seams unattached (as shown in FIG. 2) by gripping the garment at the side edges in both the first and second waist regions 54, 56. For a garment 10 such as those described with reference to FIGS. 1 and 2, the theoretical total contracting force is essentially the sum of the contracting forces of each of the stomach elastics 3 and the waist elastics 5.

In a preferred embodiment, the cloth-like laminated elastic assembly 52 of the present invention is produced by attaching stomach elastics 3 comprising manufactured elastic fibers, such as spandex fibers, having a decitex of less than about 600 or less to the first and second carrier layers 32, 32.' Most preferably, the stomach elastics 3 have a decitex of about 220. The stomach elastics 3 are arranged in parallel, and are spaced apart at about 1 to about 10 elastics per centimeter, and most preferably about 4 elastics per centimeter. It has been found that this selection of elastic strand strength and density provides good comfort and grip on the wearer, particularly when arranged to provide a total contracting force of about 3,850 grams when installed in a garment (and in conjunction with the garment's waist elastics 5, if any), but other variations may also be suitable for use with the present invention. In particular, if greater strength elastic strands are used, then a lower density may be desirable, and vice versa. It is also envisioned that the strength or density of the elastics may be increased or decreased without changing the other variables; for example, the elastic strength may be increased to provide greater overall contracting force for an adult garment, while keeping the density the same. A preferred spandex material is Lycra™ XA™ spandex elastic strand (available from E.I. DuPont de Nemours and Co., of Wilmington, Del.). For example, 220 decitex spandex fiber is available from DuPont under vendor code T262P. Of course, other materials may be used, and their decitex values adjusted accordingly to provide the desired results. For example, natural rubber has a lower spring constant than spandex, and therefore if natural rubber stomach elastics 3 are used, the decitex or density of the elastics may be increased to provide the desired overall properties.

In a preferred embodiment, the stomach elastics 3 are extended to about 2 times to 4 times, and most preferably 3.5 times their unstretched length when they are installed into the elastic assembly 52. (Due to inconsistent conventions used within the industry, an extension to 3.5 times the unstretched length is variously referred to as both 250% and 350% elongation. For clarity, the latter convention is used herein; i.e., 350% elongation equals extension to 3.5 times the relaxed length, or stated differently, 350% elongation equals extension to 350% of the original length.) When installed into a youth's pull-up type garment 10 in which the waist regions 54, 56 have lateral sides 66, 68 that are about 40 mm wide (along the lateral axis 102), this amount of extension has been found to provide the garment 10 with good stretchability and fitment for a variety of different size wearers. Of course, the amount of stretch can be varied depending on the desired wearer size range and garment geometry, as will be understood by those of ordinary skill in the art, and such variations are within the scope of the invention.

The total number of stomach elastics 3 can vary, depending on the desired total width of the elastic assembly 52. In one embodiment, in which the elastic assembly has a width of about 8 cm to 30 cm, about 8 to 300 stomach elastics 3 can be used. In an embodiment with a 12 cm width that 49 stomach elastics 3 are used. Of course, the overall width of the elastic assembly can vary, depending on the application in which it is intended to be used. It is also possible to vary the width of the elastic assembly 52 along its length, or vary the number and/or density of stomach elastics 3 along the length of the elastic assembly 52 to obtain an elastic assembly 52 having elastic properties that vary as a function of length.

It has been found that it is desirable to have the basis weights of the first and second carrier layers 32, 32' be as light as possible, without becoming so weak that they can not be processed, particularly after being severed to cut the stomach elastics 3 in the inelastic region 64, if one is used. It is also desirable to use a highly pliable material for the carrier layers 32, 32' to improve the overall softness of the elastic assembly 52. Preferably, the first and second carrier layers 32, 32' each comprise a polypropylene nonwoven SMS (spunbond-meltblown-spunbond laminate) material, and each has a basis weight of about 20.0 grams per square meter (gsm) or less, and more preferably of about 13.5 gsm or less. Suitable materials for the first and second carrier layers 32, 32' are available from Avgol Nonwoven Industries of Holon, Israel. It has been discovered that by using these basis weight carrier layers 32, 32', the elastic assembly 52 garment can achieve a more cloth-like appearance and feel. In another embodiment, the carrier layers 32, 32' may have dissimilar basis weights (i.e., one is heavier than the other), in which case it is preferred that the average basis weight of the carrier layers 32, 32' be less than about 40 gsm, and more preferably less than about 27 gsm.

In order to improve the cloth-like feel of the elastic assembly 52, the carrier layers 32, 32' are adhered to one another essentially only by a coating of adhesive that is applied to the stomach elastics 3 in the glued zones G (see FIG. 8) of the elastic assembly 52. The glued zones G ultimately form the elasticized portion or portions of the elastic assembly 52. In a preferred embodiment, the stomach elastics 3 are coated, such as by methods described elsewhere herein, with about 0.0180 grams per linear meter (gpm) of each elastic, and more preferably about 0.0121 gpm or less, when the elastics are stretched prior to installation. It will be appreciated that the grams per linear meter adhesive weight measurement is based only on the length of the portion of the stomach elastics 3 that are actually coated with adhesive, and as measured when the elastic is extended in preparation for being installed into the elastic assembly 52 and/or garment 10. As such, if the stomach elastics 3 are intermittently coated only along a portion of their length to form glued zones G and unglued zones U, as described elsewhere herein, then the uncoated length of the stomach elastics 3 is not counted when determining the weight of adhesive per unit length of the elastics. It will also be appreciated that this measurement is based on the extended length of the stomach elastics 3 (i.e., the length to which they are extended when they are installed between the carrier layers 32, 32').

In a preferred embodiment, the stomach elastics 3 are applied to the carrier layers 32, 32' using an intermittent adhesive pattern, as shown in FIGS. 7 and 8A–8C, to form a continuous supply of elastic assemblies 52 that are attached to one another end-to-end. This continuous supply of elastic assemblies 52 is preferably attached to a chassis layer web, as described with reference to FIG. 10, then severed as the individual garments 10 are severed from the continuous web of material. It is also envisioned that the elastic assemblies 52 be manufactured in other fashions, such as by severing individual elastic assemblies 52 from a continuous supply before they are attached to garments, as will be appreciated by those of ordinary skill in the art.

In a preferred embodiment, that is suitable for use in baby training pants, each individual elastic assembly 52 has a total uncontracted length (in the lateral axis 102 of the garment 10) of about 38 cm. In this preferred embodiment, the elastic assembly 52 has two elasticized glued zones G located at each end of the assembly 52, with an unglued zone U between them. Each glued zone G has a length of about 14 cm when extended and about 4.5 cm when contracted. The unglued zone U has a length of about 10 cm. Portions of the glued zones G adjacent the longitudinal ends of the elastic assembly 52 may ultimately be used as part of the side seams 48' of the garment 10, as shown in FIG. 12, in which case they may be rendered substantially inelastic by the bonding process that forms the side seams 48'. A seam width (in the longitudinal axis 100 of the garment 10) of about 1 cm is typical. The preferred adhesive for the present invention is elastic attachment adhesive provided by H.B. Fuller Company of St. Paul, Minn., under the name HL 1486UZP, but any other suitable adhesive may be used, as will be appreciated by those of ordinary skill in the art.

Although it is preferred to minimize the amount of adhesive used to attach the carrier layers 32, 32' to one another in the elasticized portions, it may not be necessary to take such care in those portions of the elastic assembly 52 that are not elasticized. This is because the elastic assembly 52, when integrated into an absorbent garment 10, may be positioned such that the elastic portions are relatively close to the wearer, while the inelastic portion 64 (as shown in FIG. 2A) may be insulated from the wearer of the garment by the interposed absorbent core assembly 50. As such, it is envisioned that the carrier layers 32, 32' may be adhered to one another by additional adhesives, heat bonding, ultrasonic bonding or other attachment methods in the unglued zone U (see FIG. 8).

When the stomach elastics 3 are elastically relaxed (i.e., contracted), the carrier layers 32, 32' in the elasticized portions of the elastic assembly 52 gather, or "shirr," into a rippled or corrugated structure. It has been discovered that, with the combination of the proper selection of stomach elastic decitex and spacing, carrier layer material and adhesive application, the elasticized portions of the elastic assembly 52 can simulate a cloth structure, both when contracted and while in various stages of extension. One aspect of the invention that provides a cloth-like structure is the manner in which the elastic assembly 52 forms a relatively high number of relatively low-thickness corrugations when it is contracted. In contrast, previously known elastic laminate structures, particularly those that have heavier and more spaced-apart elastic strands, such as the structure shown in FIG. 14, can not provide the desired corrugation thickness and frequency. Another aspect of the invention that provides a cloth-like structure is the fact that the carrier layers 32, 32' are not directly adhered to one another, but are instead joined together by a coating of adhesive on the stomach elastics 3. This allows the two carrier layers 32, 32' to move independently, reducing the "plywood effect" and making the structure softer and more pliable. Prior art garments have failed to recognize the significant advantage that can be obtained by combining closely spaced elastics and the adhesive attachment configuration provided by the present invention.

Figure 13:
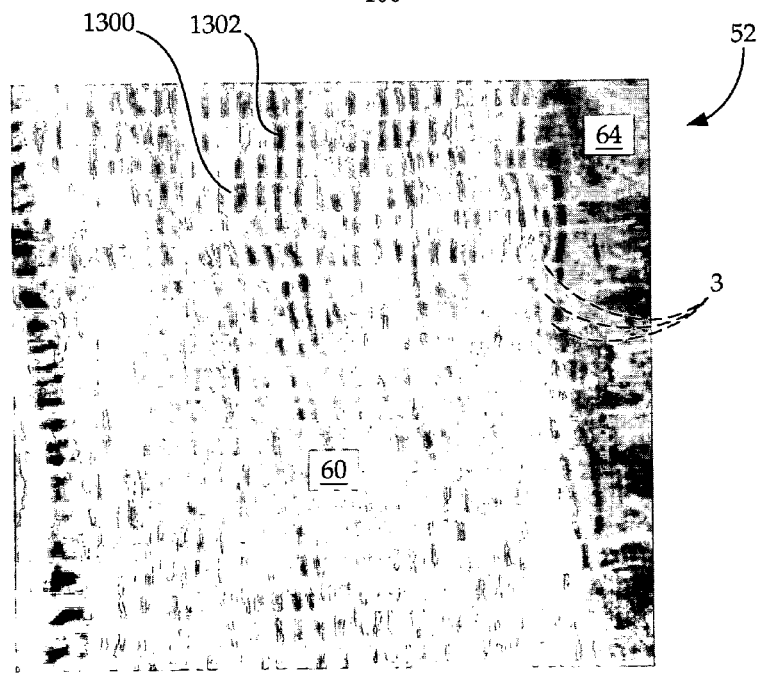
FIG. 13 is an enlargement of the photograph of FIG. 12 showing various features in greater detail.

The structure of one embodiment of the present invention is shown in more detail in FIG. 13, which is an enlarged view of a portion of the first end 60 of the elastic assembly shown in FIG. 12. FIG. 13 shows how the carrier layers 32, 32' forms a number of closely-spaced corrugations 1300 that are separated by channels 1302. The corrugations 1300 are ridges that rise above the plane of the stomach elastics 3, while the channels 1302 are portions of the carrier layer that are lower than the adjacent corrugations, and which may be above, below or in the plane of the stomach elastics 3. Because the carrier layers 32, 32' are not directly adhered to one another, it will be appreciated that the corrugations 1300 and channels 1302 of one carrier layer do not necessarily correspond to an opposite structure of the other carrier layer. That is, a corrugation 1300 in one carrier layer does not necessarily correspond to a channel in the other carrier layer (as viewed from the other side of the elastic assembly 52), and the corrugations 1300 (or channels 1302) of one carrier layer may instead be directly opposite a corrugation 1300 (or channel 1302) in the other carrier layer. This is in contrast to conventional structures in which the carrier layers 32, 32' are directly attached to one another, and the corrugations on one side of the assembly correspond to channels on the other side.

In a preferred embodiment, the cloth-like elastic assembly 52 is achieved by providing at least about 8 corrugations per centimeter or more when the elastic assembly 52 is in an elastically contracted state. Also in this embodiment, the elasticized portion of the elastic assembly 52 has a thickness of about 2.6 mm or less when compressed at a pressure of 0.05 p.s.i. and in an elastically contracted state. It is also preferable for the elasticized portion of the elastic assembly 52 to have a thickness of about 2.2 mm or less when compressed at a pressure of 0.12 p.s.i. and in an elastically contracted state. It has been found that increasing the amount of corrugations and reducing the thickness generally provide a more cloth-like garment.

It is also preferred that the elastic assembly 52 maintains its cloth-like look and feel when installed into a garment 10. If excessive bonding is used to attach the elastic assembly 52 to the garment 10, such as by applying too much adhesive, then the overall stiffness of the garment 10 plus the elastic assembly 52 may lose its cloth-like look and feel. Conversely, if too little bonding is used, the structure may become delaminated during use.

It has been found that a preferred elastic assembly 52, such as those described above, can be successfully integrated into the waist regions 54, 56 (or a single waist region) of a garment 10 without losing its cloth-like properties by attaching the elastic assembly 52 to the chassis layer 34 with a continuous meltblown fiber pattern of hot melt adhesive, applied at an amount of about 4.50 gsm or less. A preferred adhesive if H.B. Fuller's construction adhesive number 8150. A preferred method of applying the adhesive is by using a Control Coat™ system, as provided by Nordson Corporation of Norcross, Ga. Once installed, the chassis layer 34 generally conforms to the corrugated shape of the elasticized portions of the elastic assembly 52.

In a preferred embodiment, in which the elastic assembly 52 is installed on the interior body-facing side of the chassis layer 34, the body-facing portion of the elastic assembly 52 has at least about 8 corrugations per centimeter or more (when contracted), while the outward-facing portion of the chassis layer 34 opposite the elastic assembly 52 has about 10 corrugations per centimeter or more (when contracted). Also in this embodiment, the combined thickness of the chassis layer 34 and the elasticized portion of the elastic assembly 52 has a thickness of about 3.6 mm or less when compressed at a pressure of 0.05 p.s.i. (when elastically contracted), and a thickness of about 3.2 mm of less when compressed at a pressure of 0.12 p.s.i. (when elastically contracted).

Table 1 provides a comparison of the present invention with prior art garments with respect to the cloth-like qualities described above. It can be seen from Table 1, that the present invention provides thickness and corrugation frequency values that are superior to conventional products. With respect to the Kimberly Clark brand PULL UPS garment, although this product provides similar thicknesses and corrugation as the present invention, the carrier layers 32, 32' of this product are not bonded solely by adhesive applied to the elastics, and thus this product has a harsher feel and less of a cloth-like appearance than the present invention.

The following Examples are illustrative only and are not intended to limit the scope of the present invention. These examples are particularly illustrative of the benefit of reduced adhesive use that is provided by the present invention.

EXAMPLE 1

A test garment was constructed according to methods described herein and compared with a conventional garment to determine their relative comfort and cost. Both the test garment and the conventional garment were constructed to be substantially similar to the embodiment disclosed in FIGS. 1 and 2A, and each had stomach elastics 3, waist elastics 5, and gather elastics 6.

The stomach elastic assemblies 52 of the conventional garment each comprised sixteen stomach elastics 3, each made from a 610 denier (680 decitex) Lycra™ XA™ spandex elastic strand (available from E.I. DuPont de Nemours and Co., of Wilmington, Del.) that were disposed between first and second carrier layers 32, 32' to be substantially parallel to the lateral direction 102 of the garment 10 and substantially evenly spaced from one another. The total distance between the stomach elastics 3 was approximately 99 mm in the longitudinal direction 100. The carrier layers 32, 32' each comprised a sheet of Polybond™ nonwoven material (available from Polymer Group, Incorporated (PGI), headquartered in North Charleston, S.C.), having a basis weight of approximately 16 grams per square meter (g/m$^2$). The stomach elastics 3 were stretched to about 350% of their original length prior to being incorporated into the stomach elastic assemblies 52. The stomach elastics 3 were discretely coated with adhesive prior to placement between the carrier layers 32, 32' and were severed in the unglued regions U, as shown in FIG. 8, and described herein with reference to FIGS. 7–10 after being incorporated into the stomach elastic assemblies 52. About 0.63 grams of HL 1486UZP hot melt adhesive was applied to the stomach elastics 3 of the stomach elastic assemblies 52 using conventional Nordson ATS Series 6-head adhesive applicators (available from Nordson Corporation of Norcross, Ga.). The conventional adhesive applicators (one for each stomach elastic assembly 52) projected a spiral spray pattern from each head of the applicator having a width of about 22.3 mm. The six heads of each applicator were spaced apart from one another (the pitch distance) by about 22.3 mm.

TABLE 1

Comparison of Cloth-Like Garment Features[1]

| Garment | Thickness @ 0.05 psi (mm) | Thickness @ 0.12 psi (mm) | Corrugations per cm (Outside) | Corrugations per cm (Inside) |
|---|---|---|---|---|
| Present Invention (elastic assembly only) | 2.6 (0.2) | 2.2 (0.2) | | |
| Present Invention (garment) | 3.6 (0.3) | 3.2 (0.3) | 10.0 (1.0) | 8.8 (1.2) |
| Tyco brand TP02 (elastic assembly only) | 4.2 (0.3) | 3.6 (0.3) | | |
| Tyco brand TP02 (garment) | 5.5 (0.8) | 4.5 (0.5) | 3.9 (1.0) | 4.3 (1.0) |
| Kimberly Clark brand PULL UPS ™ | 1.7 (0.1) | 1.5 (0.1) | 17.4 (3.8) | 17.1 (3.0) |
| Kimberly Clark brand DEPENDS PROT. UNDERWEAR ™ | 3.0 (0.2) | 2.7 (0.2) | 3.1 (0.3) | 3.1 (0.3) |
| Procter & Gamble brand EASY UPS ™ | 1.6 (0.3) | 1.2 (0.2) | n/a | n/a |

[1]8 samples were measured for each data point; standard deviations are shown in parentheses Each stomach elastic assembly 52 was then adhered to the chassis layer 34 adjacent an opposite longitudinal end 4.

Three waist elastics 5 of the conventional garment were applied parallel to one another and in the lateral direction 102 in a fold along each longitudinal end 4 of the chassis layer 34. The waist elastics 5 were spaced from one another by about 9 mm. The folds completely covered the waist elastics 5 after they were applied. Each of the six waist elastics 5 comprised a 1680 denier (1867 decitex) Type S-7 Glospan™ spandex elastic strand (available from Radici Group of Fall River, Mass.). The chassis layer 34 comprised a nonwoven sheet of FQF™, available from First Quality Fibers of Hazelton, Pa., having a basis weight of approximately 20 g/m². Each set of three waist elastics 5 was extended to about 350% of its original length and coated with HL 1486UZP hot melt adhesive by the spiral spray procedure using a conventional Nordson ATS Series1-head adhesive applicator. Each applicator continuously sprayed adhesive in a spiral pattern having a width of about 25 mm to coat three of the waist elastics 5 just before they were placed on the chassis layer 34.

The gather elastics 6 of the conventional garment were incorporated substantially parallel to one another and in the longitudinal direction 100 of the garment 10 into the standing leg gathers 30. Each standing leg gather 30 had four gather elastics 6. The gather elastic 6 in each standing leg gather 30 that was closest to the topsheet comprised a 1680 denier (1867 decitex) Type S-7 Glospan™ spandex elastic strand, and the remaining three gather elastics 6 comprised 840 denier (940 decitex) Type S-7 Glospan™ spandex elastic strands. Each standing leg gather 30 was assembled separately from the rest of the garment 10 by stretching the gather elastics 6 to about 259% of their original length, continuously coating them with HL 1486UZP hot melt adhesive and placing them onto a sheet of Polybond™ nonwoven material having a basis weight of about 16 g/m². A conventional spiral spray applicator, such as those described above, was used to apply adhesive to the gather elastics 6. The sheet was then folded onto itself to encapsulate the gather elastics 6 and attached to the core assembly 50.

The remainder of the conventional garment 10 was constructed according to known methods.

A test garment was prepared in a nearly identical process as the conventional garment except that all the elastic elements were coated with adhesive according to an embodiment of the invention. In addition, each standing leg gather 30 of the test garment was constructed using seven 840 denier (940 decitex) Lycra™ XA™ spandex elastic strands as the gather elastics 6.

Adhesive was applied to the stomach elastics 3, waist elastics 5, and gather elastics 6 of the test garment by passing them through a comb applicator 400 as shown in FIG. 5. Each elastic element was completely coated with melted adhesive while in the comb, and no other adhesive was applied to join the carrier layers 32, 32' or to hold the folds in the chassis layer 34 and standing leg gathers 30.

The areas of the test garment and the conventional garment containing the elastic elements 3, 5, 6 were compared with one another by touch and manipulation to determine their relative softness and pliability. The test garment exhibited substantially more pliability and softness than the conventional garment, and the overall feel was more cloth-like than the conventional garment.

This improved pliability, softness and overall feel was due to the elimination of the "plywood effect" caused by oversprayed adhesive. The present invention practically eliminates the "plywood effect" by coating only the elastic strands, and not the underlying sheets of material. The coating on the elastic strands is sufficient to hold the elastic strands to the sheets and to thereby hold the sheets together during use. When the elastics contract, causing the garment to gather or "shirr," the sheets are free to wrinkle or fold because they are no longer bonded to one another at any location other than around the elastic strands, and are no longer subject to the "plywood effect."

In addition to providing improved softness and feel, the present invention provides a significant cost savings by reducing the amount of adhesive used to construct each garment. Tables 2 and 3 below compare the amount of adhesive required for the production of the conventional garment and the test garment.

TABLE 2

Conventional Garment - Spiral Spray Adhesive Application

| Area | # Elastic Strands per Area | Length per Strand, m | Total Strand Length, m | g Adhesive Used per Area | g Adhesive Used per m Elastic |
|---|---|---|---|---|---|
| Stomach | 32 | 0.245 | 7.84 | 0.63 | 0.0804 |
| Leg Gathers | 8 | 0.37 | 2.96 | 0.20 | 0.0676 |
| Waist | 6 | 0.375 | 2.25 | 0.33 | 0.1444 |

TABLE 3

Test Garment 1 - Comb Applicator Adhesive Application

| Area | # Elastic Strands per Area | Length per Strand, m | Total Strand Length, m | g Adhesive Used per Area | g Adhesive Used per m Elastic |
|---|---|---|---|---|---|
| Stomach | 32 | 0.245 | 7.84 | 0.28 | 0.0357 |
| Leg Gathers | 14 | 0.28 | 3.92 | 0.15 | 0.0383 |
| Waist | 6 | 0.375 | 2.25 | 0.20 | 0.089 |

A comparison of the amount of adhesive used in preparing the test garment and the conventional garment shows a reduction in adhesive usage per meter of elastic of 56% for the stomach area, 43% for the leg gathers, and 39% for the waist area. These reductions translate to direct cost savings for each article produced. Other benefits, such as reduced costs for cleaning the machinery, also accrue to one using an embodiment of the present invention.

EXAMPLE 2

A second test garment was constructed according to a preferred embodiment of the present invention and evaluated to determine the overall amount of adhesive required to manufacture the garment. The second test garment is substantially similar to the embodiment disclosed in FIGS. 1 and 2A and similar to the "present invention" garment described in Table 1.

The stomach elastic assemblies 52 of the conventional garment each comprised 49 stomach elastics 3, each made from a 220 decitex Lycra™ XA™ spandex elastic strand (available under vendor code T262P from E.I. DuPont de Nemours and Co., of Wilmington, Del.) that were disposed between first and second carrier layers 32, 32' to be substantially parallel to the lateral direction 102 of the garment 10 and substantially evenly spaced from one another. The garment had one elastic assembly 52 in each waist region 54, 56, as shown in FIG. 2, yielding a total of 98 stomach elastics 3 between the two elastic assemblies 52 (note that the number of stomach elastics 3 is counted before any subsequent cutting operations, so that a stomach elastic 3 that is severed into two or more parts is still counted as a single elastic). The chassis layer 34 comprised a spunbond-spunbond nonwoven polypropylene sheet having a basis weight of about 17 gsm (provided by PGI Nonwovens Polymer Group Inc. of Mooresville, N.C.). The first and second carrier layers each comprises a spunbond-meltblown-spunbond nonwoven polypropylene sheet having a basis weight of about 13.5 gsm (provided by Avgol Nonwoven Industries of Holon, Israel).

The stomach elastics 3 of each elastic assembly 52 covered a length of about 100 mm in the longitudinal direction 100 of the garment (i.e., the stomach elastics 3 covered about 100 mm of the width of the elastic assembly 52). The stomach elastics 3 were stretched to about 3.5 times their original length (350%) prior to being incorporated into the stomach elastic assemblies 52. The stomach elastics 3 were discretely coated in the glued zones G with adhesive prior to placement between the carrier layers 32, 32' and were severed in the unglued regions U after being incorporated into the stomach elastic assemblies 52, as shown in FIG. 8C. With this construction, each elastic assembly 52 had two elasticized regions, one located at each end of the elastic assembly 60, 62, as shown in FIG. 2. The total width of the garment 10, excluding the seams, 48, was about 345 mm, and thus the elastic assemblies 52 each had a length of about 345 mm. The unglued zone U of each elastic assembly 52 extended across about 100 mm in the lateral direction 102 of the garment (i.e., 100 mm along the length of the elastic assembly 52), and the glued zones G comprised the remaining portions of the elastic assembly 52. As such, only about 245 mm of each stomach elastic 3 was coated with adhesive (i.e., 345 mm total width−100 mm unglued zone width=245 mm glued zone G).

About 0.0121 grams per linear meter of HL 1486UZP hot melt adhesive was applied to each stomach elastic 3. Again, as noted before, this measurement of grams per linear meter is determined when the elastic is stretched, and includes only the length of the elastic that is actually coated, and ignores the length that is not coated (including the uncoated length of elastic would artificially decrease the apparent amount of adhesive used). As with Example 1, the adhesive was applied using a comb applicator, as described herein. No additional adhesive was used to bond the first and second carrier layers 32, 32' together. The total amount of adhesive used to apply the stomach elastics 3 to the garment 10 was about 0.290 grams (98 strands×0.245 mm glued length/strand×0.0121 gpm). This is a significant improvement over conventional adhesive applications techniques, which, as shown with reference to the conventional garment described in Example 1, require about 0.63 grams of adhesive to apply the stomach elastics 3.

The second exemplary garment was also provided with three waist elastics 5 per waist region 54, 56, for a total of six waist elastics. Each set of three waist elastics 5 comprised one 1100 decitex Lycra™ elastic strand (available from DuPont) positioned between two 800 decitex Lycra™ elastic strands (also available from DuPont). Similar reductions in the amount of adhesive required to apply the waist elastics were provided by the present invention.

The garment of Example 2 provided surprising and unexpected improved softness and feel—over both the conventional garment and the test garment of Example 1—and, like the previous example, provided a significant cost savings by reducing the amount of adhesive used to construct each garment. Table 4 below summarizes the amount of adhesive required for the second test garment.

TABLE 4

Test Garment 2 - Comb Applicator Adhesive Application

| Area | # Elastic Strands per Area | Length per Strand, m | Total Strand Length, m | g Adhesive Used per Area | g Adhesive Used per m Elastic |
|---|---|---|---|---|---|
| Stomach | 98 | 0.245 | 24.01 | 0.290 | 0.012 |
| Leg Gathers | 14 | 0.270 | 3.78 | 0.212 | 0.056 |
| Waist | 6 | 0.375 | 2.25 | 0.20 | 0.089 |

It is notable that, despite more than tripling the number of stomach elastics 3 of the second test garment over the first test garment (from 32 to 98), there is only a minor increase in the total amount of adhesive required to attach the stomach elastics 3 (from 0.280 grams to 0.290 grams). This is due, at least in part, to the fact that the stomach elastics 3 of the second test garment are significantly lighter than those of the first test garment (220 decitex versus 680 decitex). The lighter stomach elastics 3 of the second test garment each have a lower contracting force, which allows them to be held in place between the carrier layers 32, 32' by almost a third of the amount of adhesive.

Other embodiments, uses, and advantages of the invention will be apparent to those skilled in the art from consideration of the specification and practice of the invention disclosed herein. The specification should be considered exemplary only, and the scope of the invention is accordingly intended to be limited only by the following claims and equivalents thereof. To the extent that the material compositions, shapes, sizes, dimension and properties that are the subject matter of the following claims are subject to normal manufacturing variations, it will be appreciated by those of ordinary skill in the art that the claims are intended to cover such variations.

We claim:

1. An elastic assembly for absorbent garments comprising:
    a first carrier layer;
    a second carrier layer;
    an elastic layer attached between the first and second carrier layers to impart elasticity to an elasticized portion of the elastic assembly, the elastic layer comprising elastic strands having a decitex of about 600 or less, the elastic strands being arranged generally in parallel with one another and with a spacing of about 1 to about 10 elastic strands per centimeter;
    wherein the elasticized portion, when in an elastically relaxed state, has a thickness of about 2.6 mm or less at a pressure of 0.05 p.s.i.;
    wherein the elasticized portion, when in an elastically relaxed state, has about 8 or more corrugations per centimeter;
    wherein the elasticized portion comprises: a first elasticized region in which a first portion of the elastic layer is located; and a second elasticized region in which a second portion of the elastic layer is located; and wherein the elastic assembly further comprises an inelastic region, located between the first and second elasticized regions, in which a third portion of the elastic layer is located between and substantially unattached to the first and second carrier layers and severed, such that the third portion of the elastic layer does not impart substantial elasticity to the elastic assembly in the inelastic region, said first and second carrier layers being bonded to one another at the point of severance; and wherein the first and second carrier layers are gas pervious non-woven materials attached to one another in the elasticized portion substantially only by coating of adhesive on the elastic strands.

2. The elastic assembly of claim 1, wherein the coating of adhesive comprises about 0.0180 grams or less of adhesive per linear meter of each elastic strand.

3. The elastic assembly of claim 1, wherein the coating of adhesive comprises about 0.0121 grams or less of adhesive per linear meter of each elastic strand.

4. The elastic assembly of claim 1, wherein the elastic assembly has a width of about 8 cm to about 30 cm and the elastic strands comprise about 8 to about 300 elastic strands.

5. The elastic assembly of claim 1, wherein the elastic assembly has a width of about 12 cm and the elastic strands comprise about 49 elastic strands.

6. The elastic assembly of claim 1, wherein the first and second carrier layers each comprise a nonwoven material having a basis weight of less than about 20 gsm or less.

7. The elastic assembly of claim 1, wherein the first and second carrier layers each comprise a nonwoven material having a basis weight of less than about 13.5 gsm or less.

8. The elastic assembly of claim 1, wherein the elasticized portion, when in an elastically relaxed state, has a thickness of about 2.2 mm or less at a pressure of 0.12 p.s.i.

9. The elastic assembly of claim 1, wherein the elastic strands have a decitex of about 220 or less.

10. The elastic assembly of claim 1, wherein the elastic strands have a spacing of about 4 strands per centimeter.

11. The elastic assembly of claim 1, wherein the third portion of the elastic layer is severed by an ultrasonic bond, a heat bond or a mechanical bond in the inelastic region.

12. The elastic assembly of claim 1, wherein the third portion of the elastic layer is severed by a one-dimensional pattern of cuts in the inelastic region.

13. The elastic assembly of claim 1, wherein the third portion of the elastic layer is severed by a two-dimensional pattern of cuts in the inelastic region.

14. The elastic assembly of claim 1, wherein the elastic assembly is attached to an article chosen from the group consisting of: a baby training pant, a baby diaper and an adult incontinent product.

15. An absorbent garment comprising:
a first waist region;
a second waist region;
a crotch region extending between the first and second waist regions;
a core assembly located at least partially within the crotch region, the core assembly comprising a substantially fluid-pervious body-facing topsheet, a substantially fluid-impervious backsheet and an absorbent core between the topsheet and the backsheet;
at least one elastic assembly located in at least one of the first waist region and second waist region, the at least one elastic assembly comprising: a first carrier layer; a second carrier layer; an elastic layer attached between the first and second carrier layers to impart elasticity to an elasticized portion of the garment, the elastic layer comprising elastic strands having a decitex of about 600 or less, the elastic strands being arranged generally in parallel with one another and with a spacing of about 1 to about 10 elastic strands per centimeter;
wherein the elasticized portion, when in an elastically relaxed state, has a thickness of about 3.6 mm or less at a pressure of 0.05 p.s.i.;
wherein the elasticized portion, when in an elastically relaxed state, has about 8 or more corrugations per centimeter;
wherein the elasticized portion comprises: a first elasticized region in which a first portion of the elastic layer is located; and a second elasticized region in which a second portion of the elastic layer is located; and wherein the at least one elastic assembly further comprises an inelastic region, located between the first and second elasticized regions, in which a third portion of the elastic layer is located between and substantially unattached to the first and second carrier layers and severed, such that the third portion of the elastic layer does not impart substantial elasticity to the at least one elastic assembly in the inelastic region, said first and second carrier layers being bonded to one another at the point of severance; and
wherein the first and second carrier layers are gas pervious non-woven materials attached to one another in the elasticized portion substantially only by a coating of adhesive on the elastic strands.

16. The absorbent garment of claim 15, wherein the coating of adhesive comprises about 0.0180 grams or less of adhesive per linear meter of each elastic strand.

17. The absorbent garment of claim 15, wherein the coating of adhesive comprises about 0.0121 grams or less of adhesive per linear meter of each elastic strand.

18. The absorbent garment of claim 15, wherein the at least one elastic assembly has a width of about 8 cm to about 30 cm and the elastic strands comprise about 8 to about 300 elastic strands.

19. The absorbent garment of claim 15, wherein the at least one elastic assembly has a width of about 12 cm and the elastic strands comprise about 49 elastic strands.

20. The absorbent garment of claim 15, wherein the first and second carrier layers each have a basis weight of less than about 20 gsm.

21. The absorbent garment of claim 15, wherein the first and second carrier layers each have a basis weight of less than about 13.5 gsm.

22. The absorbent garment of claims 15, wherein the elasticized portion, when in an elastically relaxed state, has a thickness of about 3.2 mm or less at a pressure of 0.12 p.s.i.

23. The absorbent garment of claim 15, wherein the elastic strands have a decitex of about 220 or less.

24. The absorbent garment of claim 15, wherein the elastic strands have a spacing of about 4 strands per centimeter.

25. The absorbent garment of claim 15, wherein the garment has a total contracting force of about 3,500 grams to about 4,100 grams.

26. The absorbent garment of claim 15, wherein the garment has a total contracting force of about 3,850 grams.

27. The absorbent garment of claim 15, wherein the third portion of the elastic layer is severed by an ultrasonic bond, a heat bond or a mechanical bond in the inelastic region.

28. The absorbent garment of claim 15, wherein the third portion of the elastic layer is severed by a one-dimensional pattern of cuts in the inelastic region.

29. The absorbent garment of claim 15, wherein the third portion of the elastic layer is severed by a two-dimensional pattern of cuts in the inelastic region.

30. The absorbent garment of claim 15, wherein the absorbent garment is an article chosen from the group consisting of: a baby training pant, a baby diaper and an adult incontinent product.

* * * * *